(12) United States Patent
Wiesner et al.

(10) Patent No.: US 8,903,308 B2
(45) Date of Patent: *Dec. 2, 2014

(54) SYSTEM AND METHOD FOR PATIENT IDENTIFICATION IN A REMOTE MONITORING SYSTEM

(75) Inventors: Joel D. Wiesner, St. Peters, MO (US); Robert B. Gaines, Lake Saint Louis, MO (US)

(73) Assignee: Covidien LP, Mansfield, MA (US)

( * ) Notice: Subject to any disclaimer, the term of this patent is extended or adjusted under 35 U.S.C. 154(b) by 474 days.
This patent is subject to a terminal disclaimer.

(21) Appl. No.: 13/334,447

(22) Filed: Dec. 22, 2011

(65) Prior Publication Data

US 2012/0185268 A1 Jul. 19, 2012

Related U.S. Application Data

(63) Continuation-in-part of application No. 13/006,769, filed on Jan. 14, 2011.

(51) Int. Cl.
| | | |
|---|---|---|
| *H04W 24/00* | (2009.01) | |
| *H04W 48/18* | (2009.01) | |
| *G06Q 50/22* | (2012.01) | |
| *H04W 40/02* | (2009.01) | |
| *H04W 88/04* | (2009.01) | |
| *H04L 12/707* | (2013.01) | |

(52) U.S. Cl.
CPC ............. *H04W 48/18* (2013.01); *G06Q 50/22* (2013.01); *H04W 40/02* (2013.01); *H04W 88/04* (2013.01); *H04L 45/22* (2013.01); *H04W 24/00* (2013.01)
USPC .................... 455/11.1; 455/7; 455/9; 455/15; 455/16; 455/41.1

(58) Field of Classification Search
CPC ... H04M 1/7253; H04W 24/00; H04W 40/02; H04W 48/18; H04W 4/008; H04W 76/02; H04W 76/021; H04W 88/04
USPC ............................ 455/7, 9, 15, 16, 41.1, 11.1
See application file for complete search history.

(56) References Cited

U.S. PATENT DOCUMENTS

| | | | |
|---|---|---|---|
| 5,451,839 | A | 9/1995 | Rappaport et al. |
| 5,936,539 | A | 8/1999 | Fuchs |

(Continued)

FOREIGN PATENT DOCUMENTS

| | | |
|---|---|---|
| CA | 2 644 695 | 1/2004 |
| CA | 2 648 885 | 11/2007 |

(Continued)

OTHER PUBLICATIONS

European Comments on Written Opinion dated Nov. 8, 2013; for EP Pat. App. No. 12708203.0; 2 pages.

(Continued)

*Primary Examiner* — Bobbak Safaipour
(74) *Attorney, Agent, or Firm* — Lisa E. Winsor, Esq.

(57) ABSTRACT

A patient monitoring system for remote monitoring of medical devices. The system includes a medical device, a patient identification device and a wireless relay module. The relay module receives patient identification information from the patient identification device and medical device identification from the medical device via a wireless relay network, and transmits this information to the remote monitoring device via an internet-accessible wireless communications network. The remote monitoring device returns an acknowledgement status to the relay module, which the relay module transmits to the medical device. Upon receipt of an acknowledgment status indicating that the patient's use of the medical device is authorized, the medical device transmits medical device data to the relay module via the wireless relay network, and the relay module relays the medical device data to the remote monitoring device via the internet-accessible wireless communications network.

28 Claims, 9 Drawing Sheets

(56) References Cited

U.S. PATENT DOCUMENTS

| | | |
|---|---|---|
| 6,221,012 B1 | 4/2001 | Maschke et al. |
| 6,377,162 B1 | 4/2002 | Delestienne et al. |
| 6,377,806 B1 | 4/2002 | Tokuyoshi |
| 6,442,433 B1 | 8/2002 | Linberg |
| 6,519,569 B1 | 2/2003 | White et al. |
| 6,578,002 B1 | 6/2003 | Derzay et al. |
| 6,790,198 B1 | 9/2004 | White et al. |
| 6,839,753 B2 | 1/2005 | Biondi et al. |
| 7,028,182 B1 | 4/2006 | Killcommons |
| 7,050,984 B1 | 5/2006 | Kerpelman et al. |
| 7,082,460 B2 | 7/2006 | Hansen et al. |
| 7,178,149 B2 | 2/2007 | Hansen |
| 7,185,014 B1 | 2/2007 | Hansen |
| 7,236,936 B2 | 6/2007 | White et al. |
| 7,294,105 B1 | 11/2007 | Islam |
| 7,316,648 B2 | 1/2008 | Kelly |
| 7,349,947 B1 | 3/2008 | Slage et al. |
| 7,508,787 B2 | 3/2009 | Doshi et al. |
| 7,529,561 B2 | 5/2009 | Heinonen et al. |
| 7,539,532 B2 | 5/2009 | Tran |
| 7,539,533 B2 | 5/2009 | Tran |
| 7,558,622 B2 | 7/2009 | Tran |
| 7,613,169 B2 | 11/2009 | Vaittinen et al. |
| 7,645,258 B2 | 1/2010 | White et al. |
| 7,707,047 B2 | 4/2010 | Hasan et al. |
| 7,733,224 B2 | 6/2010 | Tran |
| 7,749,164 B2 | 7/2010 | Davis |
| 7,752,058 B2 | 7/2010 | Sasaki et al. |
| 7,827,040 B2 | 11/2010 | Brown |
| 7,873,772 B2 | 1/2011 | Waldhoff et al. |
| 7,937,370 B2 | 5/2011 | Hansen |
| 7,942,844 B2 | 5/2011 | Moberg et al. |
| 7,949,404 B2 | 5/2011 | Hill |
| 7,978,062 B2 | 7/2011 | LaLonde |
| 8,002,701 B2 | 8/2011 | John et al. |
| RE42,934 E | 11/2011 | Thompson |
| 8,073,008 B2 | 12/2011 | Mehta et al. |
| 8,095,381 B2 | 1/2012 | Simons et al. |
| 8,108,543 B2 | 1/2012 | Hansen |
| 8,125,318 B2 | 2/2012 | Heimbrock et al. |
| 8,126,728 B2 | 2/2012 | Dicks et al. |
| 8,126,729 B2 | 2/2012 | Dicks et al. |
| 8,126,730 B2 | 2/2012 | Dicks et al. |
| 8,126,732 B2 | 2/2012 | Dicks et al. |
| 8,126,733 B2 | 2/2012 | Dicks et al. |
| 8,126,734 B2 | 2/2012 | Dicks et al. |
| 8,126,735 B2 | 2/2012 | Dicks et al. |
| 8,131,564 B2 | 3/2012 | Dicks et al. |
| 8,131,565 B2 | 3/2012 | Dicks et al. |
| 8,131,566 B2 | 3/2012 | Dicks et al. |
| 8,140,356 B2 | 3/2012 | Dicks et al. |
| 8,155,982 B2 | 4/2012 | Dicks et al. |
| 8,200,195 B2 | 6/2012 | Le Saint et al. |
| 8,214,549 B2 | 7/2012 | Dicks et al. |
| 8,326,648 B2 | 12/2012 | Kenedy et al. |
| 8,373,556 B2 | 2/2013 | LaLonde et al. |
| 8,395,498 B2 | 3/2013 | Gaskill et al. |
| 8,428,722 B2 | 4/2013 | Verhoef et al. |
| 8,515,547 B2 | 8/2013 | Mass et al. |
| 8,587,427 B2 | 11/2013 | LaLonde et al. |
| 8,694,600 B2 * | 4/2014 | Gaines et al. ................ 709/217 |
| 2002/0178126 A1 | 11/2002 | Beck et al. |
| 2002/0198473 A1 | 12/2002 | Kumar et al. |
| 2004/0155772 A1 | 8/2004 | Medema et al. |
| 2004/0204743 A1 | 10/2004 | McGrath et al. |
| 2005/0010093 A1 | 1/2005 | Ford et al. |
| 2005/0185398 A1 | 8/2005 | Scannell, Jr. |
| 2005/0188853 A1 | 9/2005 | Scannell, Jr. |
| 2005/0201300 A1 | 9/2005 | Bridgelall |
| 2005/0243988 A1 | 11/2005 | Barclay et al. |
| 2005/0288571 A1 | 12/2005 | Perkins et al. |
| 2006/0154642 A1 | 7/2006 | Scannell, Jr. |
| 2006/0238333 A1 | 10/2006 | Welch et al. |
| 2007/0106126 A1 | 5/2007 | Mannheimer et al. |
| 2007/0156033 A1 | 7/2007 | Causey, III et al. |
| 2007/0180140 A1 | 8/2007 | Welch et al. |
| 2007/0186923 A1 * | 8/2007 | Poutiatine et al. ....... 128/200.14 |
| 2007/0216764 A1 | 9/2007 | Kwak |
| 2007/0230197 A1 | 10/2007 | Scannell, Jr. |
| 2007/0253380 A1 | 11/2007 | Jollota et al. |
| 2007/0254593 A1 | 11/2007 | Jollota et al. |
| 2007/0255125 A1 | 11/2007 | Moberg et al. |
| 2007/0255250 A1 | 11/2007 | Moberg et al. |
| 2007/0258395 A1 | 11/2007 | Jollota et al. |
| 2007/0268687 A1 | 11/2007 | Scannell, Jr. |
| 2007/0276270 A1 | 11/2007 | Tran |
| 2008/0004907 A1 | 1/2008 | Bayne |
| 2008/0012761 A1 | 1/2008 | Derrick et al. |
| 2008/0071234 A1 | 3/2008 | Kelch et al. |
| 2008/0097550 A1 | 4/2008 | Dicks et al. |
| 2008/0097551 A1 | 4/2008 | Dicks et al. |
| 2008/0097552 A1 | 4/2008 | Dicks et al. |
| 2008/0097793 A1 | 4/2008 | Dicks et al. |
| 2008/0097908 A1 | 4/2008 | Dicks et al. |
| 2008/0097909 A1 | 4/2008 | Dicks et al. |
| 2008/0097910 A1 | 4/2008 | Dicks et al. |
| 2008/0097911 A1 | 4/2008 | Dicks et al. |
| 2008/0097912 A1 | 4/2008 | Dicks et al. |
| 2008/0097913 A1 | 4/2008 | Dicks et al. |
| 2008/0097914 A1 | 4/2008 | Dicks et al. |
| 2008/0097917 A1 | 4/2008 | Dicks et al. |
| 2008/0108880 A1 | 5/2008 | Young et al. |
| 2008/0183502 A1 | 7/2008 | Dicks et al. |
| 2008/0224852 A1 | 9/2008 | Dicks et al. |
| 2008/0281168 A1 | 11/2008 | Gibson et al. |
| 2009/0019061 A1 | 1/2009 | Scannell, Jr. |
| 2009/0023391 A1 | 1/2009 | Falck |
| 2009/0058635 A1 | 3/2009 | LaLonde et al. |
| 2009/0058636 A1 | 3/2009 | Gaskill et al. |
| 2009/0062887 A1 | 3/2009 | Mass et al. |
| 2009/0063187 A1 * | 3/2009 | Johnson et al. ................ 705/2 |
| 2009/0063193 A1 | 3/2009 | Barton et al. |
| 2009/0073694 A1 | 3/2009 | Scannell, Jr. |
| 2009/0105549 A1 | 4/2009 | Smith et al. |
| 2009/0115628 A1 | 5/2009 | Dicks et al. |
| 2009/0128320 A1 | 5/2009 | Needham et al. |
| 2009/0184835 A1 | 7/2009 | Deaver, Sr. et al. |
| 2009/0203329 A1 | 8/2009 | White et al. |
| 2009/0234672 A1 | 9/2009 | Dicks et al. |
| 2009/0247114 A1 | 10/2009 | Sennett et al. |
| 2009/0252117 A1 | 10/2009 | Sherman et al. |
| 2009/0299788 A1 | 12/2009 | Huber et al. |
| 2009/0306747 A1 | 12/2009 | Fischer et al. |
| 2010/0011000 A1 | 1/2010 | Chakra et al. |
| 2010/0027518 A1 | 2/2010 | Wang |
| 2010/0077115 A1 | 3/2010 | Rofougaran |
| 2010/0079276 A1 | 4/2010 | Collins et al. |
| 2010/0080200 A1 | 4/2010 | Stewart |
| 2010/0082371 A1 | 4/2010 | Kamp et al. |
| 2010/0085948 A1 | 4/2010 | Yu et al. |
| 2010/0117835 A1 | 5/2010 | Nanikashvili |
| 2010/0138235 A1 | 6/2010 | Marks et al. |
| 2010/0166170 A1 | 7/2010 | East |
| 2010/0198142 A1 | 8/2010 | Sloan et al. |
| 2010/0217723 A1 | 8/2010 | Sauerwein, Jr. et al. |
| 2010/0219250 A1 | 9/2010 | Wang |
| 2010/0234695 A1 | 9/2010 | Morris |
| 2010/0260061 A1 | 10/2010 | Bojahra et al. |
| 2010/0279647 A1 | 11/2010 | Jacobs et al. |
| 2010/0292556 A1 | 11/2010 | Golden |
| 2010/0317286 A1 | 12/2010 | Jung et al. |
| 2010/0318578 A1 | 12/2010 | Treu et al. |
| 2011/0021902 A1 | 1/2011 | Kim et al. |
| 2011/0032822 A1 | 2/2011 | Soomro |
| 2011/0066555 A1 | 3/2011 | Dicks et al. |
| 2011/0078441 A1 | 3/2011 | Dicks et al. |
| 2011/0087756 A1 | 4/2011 | Biondi et al. |
| 2011/0093283 A1 | 4/2011 | Dicks et al. |
| 2011/0093284 A1 | 4/2011 | Dicks et al. |
| 2011/0093285 A1 | 4/2011 | Dicks et al. |
| 2011/0093286 A1 | 4/2011 | Dicks et al. |
| 2011/0093287 A1 | 4/2011 | Dicks et al. |
| 2011/0093297 A1 | 4/2011 | Dicks et al. |
| 2011/0148624 A1 | 6/2011 | Eaton et al. |

(56) References Cited

U.S. PATENT DOCUMENTS

| | | | |
|---|---|---|---|
| 2011/0158430 A1 | 6/2011 | Dicks et al. | |
| 2011/0161111 A1 | 6/2011 | Dicks et al. | |
| 2011/0179405 A1 | 7/2011 | Dicks et al. | |
| 2011/0255454 A1 | 10/2011 | Hauser et al. | |
| 2011/0270045 A1 | 11/2011 | Lebel et al. | |
| 2011/0273287 A1 | 11/2011 | LaLonde et al. | |
| 2011/0280224 A1 | 11/2011 | Falck et al. | |
| 2011/0282671 A1 | 11/2011 | Dicks et al. | |
| 2011/0292862 A1 | 12/2011 | Shimizu | |
| 2012/0004925 A1 | 1/2012 | Braverman et al. | |
| 2012/0108917 A1 | 5/2012 | Libbus et al. | |
| 2012/0182143 A1* | 7/2012 | Gaines et al. | 340/539.12 |
| 2012/0182894 A1* | 7/2012 | Gaines et al. | 370/252 |
| 2012/0182924 A1* | 7/2012 | Gaines et al. | 370/315 |
| 2012/0182927 A1* | 7/2012 | Wiesner et al. | 370/315 |
| 2012/0184207 A1* | 7/2012 | Gaines et al. | 455/11.1 |
| 2012/0184237 A1* | 7/2012 | Gaines et al. | 455/404.1 |
| 2012/0185268 A1* | 7/2012 | Wiesner et al. | 705/2 |
| 2012/0226768 A1* | 9/2012 | Gaines et al. | 709/217 |
| 2012/0226771 A1* | 9/2012 | Harrington et al. | 709/217 |
| 2012/0256751 A1 | 10/2012 | Nallabelli et al. | |
| 2012/0293323 A1 | 11/2012 | Kaib et al. | |
| 2013/0015966 A1 | 1/2013 | Soomro et al. | |
| 2013/0021169 A1 | 1/2013 | Soomro et al. | |
| 2013/0022022 A1 | 1/2013 | Schmitt | |
| 2013/0066644 A1 | 3/2013 | Dicks et al. | |
| 2013/0147622 A1 | 6/2013 | LaLonde et al. | |
| 2013/0154851 A1 | 6/2013 | Gaskill et al. | |
| 2013/0162426 A1* | 6/2013 | Wiesner et al. | 340/539.1 |
| 2013/0278414 A1 | 10/2013 | Sprigg et al. | |
| 2013/0310896 A1 | 11/2013 | Mass | |
| 2014/0009271 A1 | 1/2014 | Collins et al. | |
| 2014/0062718 A1 | 3/2014 | LaLonde et al. | |
| 2014/0142979 A1 | 5/2014 | Mitsunaga | |
| 2014/0152466 A1* | 6/2014 | Wiesner et al. | 340/870.07 |

FOREIGN PATENT DOCUMENTS

| | | |
|---|---|---|
| CA | 2 644 635 | 8/2008 |
| CN | 101601040 A | 12/2009 |
| EP | 2227063 A1 | 9/2010 |
| JP | 2003109160 | 4/2003 |
| JP | 2006520657 | 9/2006 |
| JP | 2007531442 | 11/2007 |
| JP | 2008108170 | 5/2008 |
| JP | 2009-535715 A | 1/2009 |
| JP | 2010-524050 A | 7/2010 |
| JP | 2011-502369 A | 1/2011 |
| KR | 10-2008-0016458 A | 2/2008 |
| KR | 10-2009-0122968 A | 12/2009 |
| KR | 10-2010-0028318 A | 3/2010 |
| WO | WO 94/16617 | 8/1994 |
| WO | WO 98/14228 A1 | 4/1998 |
| WO | WO 03/048919 A1 | 6/2003 |
| WO | WO 2004/070994 A2 | 8/2004 |
| WO | WO 2004/070994 A3 | 8/2004 |
| WO | WO 2004/084720 A2 | 10/2004 |
| WO | WO 2005/057294 A1 | 6/2005 |
| WO | WO 2005/057834 A2 | 6/2005 |
| WO | WO 2005/098736 A2 | 10/2005 |
| WO | WO 2007/124091 A1 | 11/2007 |
| WO | WO 2007/127879 A2 | 11/2007 |
| WO | WO 2008/052034 A1 | 5/2008 |
| WO | WO 2008/097316 A1 | 8/2008 |
| WO | WO 2009/032134 A2 | 3/2009 |
| WO | WO 2009/063303 A1 | 5/2009 |

OTHER PUBLICATIONS

Final Office Action dated Dec. 2, 2013; for U.S. Appl. No. 13/006,784; 38 pages.
Amendment filed Mar. 26, 2014, to Office Action dated Dec. 27, 2013; for U.S. Appl. No. 13/352,575; 12 pages.
Amendment filed Mar. 26, 2014; to Office Action dated Jan. 7, 2014; for U.S. Appl. No. 13/353,565; 15 pages.
Amendment and Response to Restriction Requirement for Office Action dated Feb. 10, 2014; filed Mar. 21, 2014; for U.S. Appl. No. 13/352,608; 7 pages.
Letter from CCPIT Patent and Trademark Law Office dated Mar. 3, 2014; for Chinese Pat. App. No. 201280011025.0; 1 page.
Chinese Voluntary Amendment (including English translation) received Mar. 3, 2014; for Chinese Pat. App. No. 201280011025.0; 16 pages.
Office Action dated May 27, 2014; for U.S. Appl. No. 13/334,463; 48 pages.
Mexican Notice of Allowance dated May 7, 2014; for Mexican Pat. App. No. MX/a/2013/009985; 2 pages.
Response filed Feb. 18, 2014 for Office Action dated Sep. 27, 2013 for U.S. Appl. No. 13/241,620; 24 pages.
Response filed Feb. 13, 2014 for Office Action dated Sep. 5, 2013 for U.S. Appl. No. 13/006,769; 18 pages.
Request for Continued Examination filed Jan. 24, 2014; for U.S. Appl. No. 13/037,886; 2 pages.
Response filed with RCE on Feb. 13, 2014 for Final Office Action dated Dec. 2, 2013 for U.S. Appl. No. 13/006,784; 24 pages.
European Response filed Mar. 3, 2014; to Official Communication dated Aug. 22, 2013; and to the Written Opinion; for European Pat. App. No. 12704944.3; 15 pages.
European Response filed Mar. 3, 2014; to Official Communication dated Aug. 22, 2013; and to the Written Opinion; for European Pat. App. No. 12701584.0; 11 pages.
PCT Search Report and Written Opinion of the ISA dated Mar. 4, 2014; for PCT Pat. App. No. PCT/US2013/059703; 12 pages.
Miche, et al., "The Internet of Vehicles or the Second Generation of Telematic Services", ERCIM News, ERCIM, Paris, FR, vol. 77, Apr. 1, 2009, pp. 43-45.
Kawai et al., "Proposal of an Assured Corridor Mechanism for Urgent Information Transmission In Wireless Sensor Networks", IEICE Trans. on Commun., vol. E90B, No. 10, Oct. 1, 2007, pp. 2817-2826, XP001508610.
International Search Report and Written Opinion of the International Searching Authority for PCT/US2012/021007, dated Sep. 20, 2012, 19 pages.
International Search Report and Written Opinion of the International Searching Authority for PCT/US2012/068895, dated Mar. 15, 2013, 15 pages.
International Search Report and Written Opinion of the International Searching Authority for PCT/US2013/020069, dated Feb. 1, 2013, 9 pages.
International Search Report and Written Opinion of the International Searching Authority for PCT/US2013/020071, dated Feb. 1, 2013, 10 pages.
International Search Report and Written Opinion of the International Searching Authority for PCT/US2012/025906, dated Dec. 3, 2012, 21 pages.
Office Action dated Nov. 16, 2012 for U.S. Appl. No. 13/037,886, filed Mar. 1, 2011, 19 pages.
Response to Office Action dated Nov. 16, 2012 for U.S. Appl. No. 13/037,886, filed Feb. 15, 2013.
Response filed Aug. 14, 2013; to Office Action dated May 15, 2013; for U.S. Appl. No. 13/006,784; 13 pages.
Atmel Corporation, "ZigBee PRO Stack and Software Development Kit," http://www.meshnetics.com/wsn-software/, Nov. 4, 2011.
Bachelder, "Hospital Tries ZigBee to Track Patients," RFID Journal, Jul. 21, 2006.
BelAir Networks, "Capacity of Wireless Mesh Networks," white paper, 2006.
Bogia, "Enabling the future of u-Health-IEEE 11073 Personal Health Device Standards," slides, Sep. 16, 2009.
Bowman, "Newly Ratified ZigBee Health Care Profile Now Available for Public Download," http://www.fiercehealthcare.com/node/40708, Apr. 6, 2010.
Craig, "ZigBee Networks," http://medicaldesign.com/electrical-components/zigbee_networks/, Apr. 1, 2005.
Craig, "ZigBee: 'Wireless Control That Simply Works'," https://docs.zigbee.org/zigbee-docs/dcn/04-1427.pdf, prior to Jan. 2011.
Digi International Inc., "ConnectPort® X4 H," retrieved from the Internet: http://www.digi.com, 2008-2010.

(56) References Cited

OTHER PUBLICATIONS

Digi International Inc., "Demystifying 802.15.4 and ZigBee®," white paper, retrieved from the Internet: http://www.digi.com, 2008-2010.
Digi International Inc., "XBee® & XBee-PRO® ZB," retrieved from the Internet: http://www.digi.com, 2008-2010.
Digi International Inc., "XBee® & XBee-PRO® ZB ZigBee® PRO RF Modules," http://www.digi.com/products/wireless/zigbee-mesh/xbee-zb-module,jsp, Nov. 2, 2010.
Dvorak, "Remote Monitoring," http://medicaldesign.com/electrical-components/remote_monitoring/index.html, Apr. 1, 2005.
ENP Newswire, "Freescale products achieve ZigBee Health Care Certification," May 19, 2010.
Huang, "Medical electronics: from hospital and clinic to the home," http://www.eetimes.com/General/DisplayPrintViewContent?contentItemid=4211247, Dec. 8, 2010.
ICP DAS, "ZigBee Converter User's Manual," Sep. 22, 2008.
Le, "Designing a ZigBee-ready IEEE 802.15.4-compliant radio transceiver," http://rfdesign.com/mag/411rfdf4.pdf, Nov. 2004.
Norris et al., "Single-chip ZigBee for Indoor Mobile Telemetry," presentation, Jun. 21, 2005.
Pinto, "WMM-Wireless Mesh Monitoring," Technical report, 2009.
Sailhan et al., "Wireless Mesh Network Monitoring: Design, Implementation and Experiments," In proc. of IEEE Workshop on Distributed Autonomous Network Management (DANMS), 2007.
Skibniewski et al, "Ubiquitous Computing: Object Tracking and Monitoring Inconstruction Processes Utilizing Zigbee™ Networks," The 23th International Symposium on Automation and Robotics in Construction (ISARC2006), Oct. 3-5, Tokyo, Japan.
Stewart, "Build reliable Zigbee-based solutions," EE Times-Asia, Apr. 16-30, 2007.
Texas Instruments, "Choose your ZigBee solution with TI," 1Q 2010.
Texas Instruments, "Consumer Medical Applications Guide," retrieved from the Internet: http://www.ti.com/medical, 2010.
Texas Instruments, "RF/IF and ZigBee® Solutions," http://focus.ti.com/analog/docs/gencontent.tsp?familyid=367&genContentid=24190&DC . . . , Dec. 8, 2010.
Texas Instruments, "ZigBee® Wireless Networking Overview," 1 page, 2010.
The Silicon Horizon Inc., "techFX Zigbee rev A-techFX Zigbee Tools v 1.0," 2007-2008.
Tutorial-Reports.com, "Zigbee Tutorial," http://www.tutorial-reports.com/book/print/152, Nov. 1, 2010.
Unknown author, "The Nokia Network Monitor Introduction," http://www.panuworld.net/nuukiaworld/misc/netmon/index.htm, Oct. 30, 2005.
Versel, "ZigBee Alliance ratifies wireless protocol for low-power medical devices," retrieved from the Internet: http://www.fiercemobilehealthcare.com, Apr. 6, 2010.
Wellspring, "Router, Gateway, Base Station, Cell Modem Specification and Submittal," http://www.h2odegree.com/documents/ReferenceLibrary/OtherProductLiterature/RouterGatewayBaseSpecSheetSubmittal.pdf, 5 pages, prior to Jan. 2011.
Wellspring, "Wellspring Switches to a ZigBee-Cellular Hybrid System," press release, Feb. 20, 2006.
ZigBee Alliance, "ZigBee Wireless Sensor Applications for Health, Wellness and Fitness," https://docs.zigbee.org/zigbee-docs/dcn/09-4962.pdf, Mar. 2009.
Response filed Jul. 12, 2013; to Final Office Action dated May 22, 2013; for U.S. Appl. No. 13/037,886; 14 pages.
Office Action; dated May 15, 2013; for U.S. Appl. No. 13/006,784; 35 pages.
Article 19 Amendment; dated Nov. 16, 2012; for PCT Pat. App. No. PCT/US2012/021007; 7 pages.
Article 19 Amendment; dated Feb. 4, 2013; for PCT Pat. App. No. PCT/US2012/025906; 9 pages.
PCT International Preliminary Report on Patentability; dated Jul. 25, 2013; for PCT Pat. App. No. PCT/US2012/021007; 12 pages.
PCT International Search Report; dated Aug. 2, 2012; for PCT Pat. App. No. PCT/US2012/021008.
PCT International Preliminary Report on Patentability; dated Jul. 25, 2013; for PCT Pat. App. No. PCT/US2012/021008; 7 pages.
PCT International Preliminary Report on Patentability of the ISA; dated Sep. 12, 2013; for PCT Pat. App. No. PCT/US2012/025906; 14 pages.
Office Action dated Dec. 27, 2013; for U.S. Appl. No. 13/352,575; 31 pages.
Office Action dated Jan. 7, 2014; for U.S. Appl. No. 13/353,565; 33 pages.
Mexican Office Action received Apr. 22, 2014; for Mexican Pat. App. No. MX/a/2013/008154; 4 pages.
Response to Office Action dated Apr. 29, 2014 for U.S. Appl. No. 13/352,608, filed Jan. 18, 2012.
Notice of Allowance dated Jun. 6, 2014 for U.S. Appl. No. 14/154,285, filed Jan. 14, 2014.
Notice of Allowance dated Jun. 9, 2014 for U.S. Appl. No. 13/006,769, filed Jan. 14, 2011.
Office Action; dated May 15, 2013; for U.S. Appl. No. 13/006,784; 37 pages.
Office Action dated May 22, 2013; for U.S. Appl. No. 13/037,886; 14 pages.
PCT Search Report and Written Opinion of the ISA; dated Apr. 1, 2013; for PCT Pat. App. No. PCT/US2012/068892; 12 pages.
PCT Search Report and Written Opinion of the ISA; dated Apr. 1, 2013; for PCT Pat. App. No. PCT/US2012/068888; 15 pages.
PCT Search Report and Written Opinion of the ISA; dated Apr. 29, 2013; for PCT Pat. App. No. PCT/US2013/021530; 10 pages.
Office Action dated Sep. 5, 2013, for U.S. Appl. No. 13/006,769, 36 pages.
Notice of Allowance; dated Oct. 9, 2013; for U.S. Appl. No. 13/037,886, 11 pages.
Notice of Allowance dated Apr. 30, 2014; for U.S. Appl. No. 13/241,620; 21 pages.
Office Action dated Apr. 29, 2014; for U.S. Appl. No. 13/352,608; 50 pages.
Mexican Official Action received May 2, 2014, for Mexican Pat. App. No. MX/A2013/008157; 3 pages.
U.S. Response to 312 Amendment dated Jul. 21, 2014; for U.S. Appl. No. 14/154,285; 3 pages.
Japanese Office Action (including English translation) dated Jun. 23, 2014; for Japanese Pat. App. No. 2013-549532 6 pages.
PCT International Preliminary Report on Patentability of the ISA dated Jul. 3, 3014; for PCT Pat. App. No. PCT/US2012/068892; 8 pages.
PCT International Preliminary Report on Patentability of the ISA dated Jul. 3, 2014; for PCT Pat. App. No. PCT/US2012/068888; 8 pages.
Singapore Written Opinion dated Jun. 18, 2014; for Singapore Pat. App. No. 2013053236; 11 pages.
Singapore Written Opinion dated Jun. 19, 2014; for Singapore Pat. App. No. 2013065230; 22 pages.
Response filed (with English Language Passage) of Mexican Office Action received Jul. 7, 2014; for Mexican Pat. App. No. MX/a/2013/008154; 16 pages.
Final Office Action dated Aug. 6, 2014; for U.S. Appl. No. 13/352,608; 38 pages.
PCT International Preliminary Report on Patentability of the ISA dated Jul. 31, 2014; for PCT Pat. App. No. PCT/US2013/020069; 6 pages.
PCT International Preliminary Report on Patentability of the ISA dated Jul. 31, 2014; for PCT Pat. App. No. PCT/US2013/020071; 6 pages.
Singapore Written Opinion dated Jul. 25, 2014; for Singapore Pat. App. No. 2013053244; 7 pages.
European Search Report dated Jun. 14, 2014; for European Patent Application No. 14168075.1-1951; 8 pages.
Office Action dated Jun. 23, 2014 for U.S. Appl. No. 13/334,459, filed Dec. 22, 2011 44 pages.
Office Action dated Jun. 16, 2014 for U.S. Appl. No. 13/353,565, filed Jan. 19, 2012.

(56) References Cited

OTHER PUBLICATIONS

Japanese Office Action dated May 30, 2014 for Application No. 2013-549531 3 pages.
Notice of Allowance for U.S. Appl. No. 13/352,575, filed Jan. 18, 2012.
Response with Terminal Disclaimer filed Jul. 30, 2014; to Office Action dated Jun. 20, 2014; for U.S. Appl. No. 13/334,447; 15 pages.
Response with Terminal Disclaimer filed Jul. 30, 2014; to Office Action dated Jun. 23, 2014; for U.S. Appl. No. 13/334,459; 13 pages.
Response filed Jul. 30, 3014; to Final Office Action dated Jun. 16, 2014; to U.S. Appl. No. 13/353,565; 22 pages.
Response filed Aug. 4, 2014; to Office Action dated May 27, 2014; for U.S. Appl. No. 13/334,463; 21 pages.
Mexican Response to Office Action received Jul. 29, 2014; for Mexican Pat. App. No. MX/a/2013/008157; 14 pages.
PCT International Preliminary Report on Patentability dated Jul. 3, 2014; for PCT Pat. App. No. PCT/US2012/068895; 10 pages.
U.S. Appl. No. 14/308,881, filed Jun. 19, 2014, Gaines, et al.

* cited by examiner

SYSTEM AND METHOD FOR PATIENT IDENTIFICATION IN A REMOTE MONITORING SYSTEM

RELATED APPLICATION

This application is a continuation-in-part of U.S. patent application Ser. No. 13/006,769, entitled "Wireless Relay Module for Remote Monitoring System" and filed on Jan. 14, 2011, and is related to U.S. application Ser. No. 13/006,784, entitled "Medical Device Wireless Network Architectures" and filed Jan. 14, 2011, each of which shares an assignee-in-common with the present application and is incorporated by reference in its entirety herein for all purposes.

FIELD OF THE INVENTION

The present invention is directed to a system and method for identifying a patient in a remote monitoring system monitoring medical devices, and more particularly, to a system and method for associating the patient with a particular medical device before remote monitoring of that medical device begins.

BACKGROUND OF THE INVENTION

In critical care and home care health service centers including hospitals, clinics, assisted living centers and the like, care giver-patient interaction time is at a premium. Moreover, rapid response times by care givers to significant health conditions and events can be critical. Systems of centralized monitoring have been developed to better manage care giver time and patient interaction. In such systems, physiological data from each patient is transmitted to a centralized location. At this centralized location, a single or small number of technicians monitor all of this patient information to determine patient status. Information indicating a patient alarm condition will cause the technicians and/or system to communicate with local care givers to provide immediate patient attention, for example via wireless pagers and/or cell phones, and/or by making a facility-wide audio page.

Implementing such centralized monitoring systems using wireless networks may present a number of difficulties. In order to effectively monitor patient status using information provided by a variety of medical devices that may be dynamically assigned to patients in a variety of rooms and on a variety of floors in a facility, it would be desirable to establish communications between the medical devices and the centralized location by means of a local area network such as, for example, a "WiFi" network based on IEEE 802.11 standards. However, as such networks are typically already in place in facilities to support a variety of other functions (for example, physician access to electronic medical records (EMRs), facility administrative systems and other functions), it is often undesirable to secure sufficient local area network access for the purpose of providing centralized monitoring. Moreover, when a patient is located remotely from a critical care health service center (for example, at home), access to traditional local area network facilities such as a WiFi network may be unavailable or not sufficiently reliable to support critical care monitoring applications.

As an alternative to conventional WiFi or IEEE 802.11-based local area networks, ZIGBEE networks based on the IEEE 802.15.4 standard for wireless personal area networks have been used for collecting information from a variety of medical devices in accordance with IEEE 11073 Device Specializations for point-of-care medical device communication, including for example pulse oximeters, blood pressure monitors, pulse monitors, weight scales and glucose meters. See, e.g., *ZIGBEE Wireless Sensor Applications for Health, Wellness and Fitness*, the ZIGBEE Alliance, March 2009, which is incorporated by reference herein in its entirety. ZIGBEE networks provide the advantage of being dynamically configurable, for example, in "self-healing" mesh configurations, and operating with low power requirements (enabling, for example, ZIGBEE transceivers to be integrally coupled to the medical devices under battery power). However, transmission ranges between individual ZIGBEE transceivers are generally limited to no more than several hundred feet. As a consequence, such networks are unusable for centralized monitoring locations located off-site. Also, in accordance with applicable patient data privacy provisions of the Health Insurance Portability and Accountability Act of 1996 (HIPAA), communication of information between the monitored medical devices and the central monitoring location must be done securely.

It is of course critical to the monitoring process that patients are accurately identified in association with the particular medical devices that they are using before treatment and monitoring begin. Challenges exist in identifying patients remotely in "real time" as care providers are about to initiate treatment, while preserving patient confidentiality and privacy (for example, in accordance with HIPAA requirements).

SUMMARY OF THE INVENTION

The present invention is directed to a patient monitoring system for remotely monitoring medical devices used by patients. The system includes at least one medical device for use on or by a patient, at least one patient identification device for identifying the patient and at least one wireless relay module for providing networked communications between at least one medical device and a remote monitoring device. The patient identification device may be, for example, formed as an integral component of, fixedly attached to, coupled (wireless or wired) or disposed separate to the medical device.

In accordance with a preferred embodiment of the invention, the one or more medical devices (including but not limited to, respirators, enteral feeding devices, pulse oximeters, blood pressure monitors, pulse monitors, weight scales and glucose meters) are provided at a patient facility. An interface circuit is coupled to each medical device, and is configured for communicating with the one or more wireless relay modules via a wireless relay network. The wireless relay modules communicate with the remote monitoring device over an internet-accessible wireless communication network, and preferably, over a wireless wide-area network (WWAN) such as a mobile telephone data network including (for example, based on a Global System for Mobile Communications (GSM) or Code Division Multiple Access (CDMA) cellular network or associated wireless data channels). For compliance with HIPAA regulations, for example, communications over each of the wireless networks are preferably conducted securely.

Each of the plurality of wireless relay modules includes a first receiver capable of wirelessly receiving medical device data from respective interface circuits via the wireless relay network, a first transmitter capable of wirelessly transmitting medical device data to another one of the wireless relay modules over the wireless relay network, a second transmitter capable of wirelessly transmitting medical device data over an internet-accessible wireless communications network, a second receiver capable of wirelessly receiving medical device data over the internet-accessible wireless communications network, a controller coupled to the first and second transmitters and receivers, and a memory device coupled to the controller. As used herein, "medical device data" and "data" as generally used herein means data from or about the medical device including, for example, medical device identification, medical device software, medical device settings or status information (including alarm information and/or alarm priority), patient identification information, patient personal identification number(s) "PIN(s)", patient prescriptions, and/or patient medical and/or physiological data as is collected, produced and/or generated by at least one of the medical device and patient identification device.

The controller is configured to determine access status of the internet-accessible wireless communications network, and to select one of the first or second transmitters based on that status. For example, when the status indicates that the internet-accessible wireless communications network is accessible to the wireless relay module, the controller selects the second transmitter for transmitting medical device data transmitted by the interface circuit to the remote monitoring device. When the status indicates that the internet-accessible wireless communications network is not accessible, the controller selects the first transmitter for transmitting the medical device data to another one of the wireless relay modules. In this manner, another attempt to transmit the medical device data over the internet-accessible wireless communication network can be attempted by this other wireless relay module (and potentially additional ones of the wireless relay modules) until a successful transmission to the remote monitoring device is achieved.

The relay module is further configured to receive identification information from the at least one patient identification device identifying a patient and identification information identifying at least one medical device via the first receiver, to transmit this information or a portion thereof to the remote monitoring device via the internet-accessible wireless communications network, to receive an acknowledgement status from the remote monitoring device via the internet-accessible wireless communications network, and to transmit the acknowledgement status to the medical device over the wireless relay network. Upon receipt of an acknowledgment status indicating that the patient's use of the medical device is authorized, the medical device is configured to transmit medical device data corresponding to an output of at least one sensor of the medical device to the relay module. The relay module relays the medical device data to the remote monitoring device over the internet-accessible wireless communications network.

BRIEF DESCRIPTION OF THE DRAWINGS

The invention will become more readily apparent from the Detailed Description of the Invention, which proceeds with reference to the drawings, in which.

DETAILED DESCRIPTION OF THE INVENTION

Reference will now be made in detail to exemplary embodiments of the invention, including the best modes contemplated by the inventors for carrying out the invention. Examples of these exemplary embodiments are illustrated in the accompanying drawings. While the invention is described in conjunction with these embodiments, it will be understood that it is not intended to limit the invention to the described embodiments. Rather, the invention is also intended to cover alternatives, modifications, and equivalents as may be included within the spirit and scope of the invention as defined by the appended claims.

In the following description, specific details are set forth in order to provide a thorough understanding of the present invention. The present invention may be practiced without some or all of these specific details. In other instances, well-known aspects have not been described in detail in order not to unnecessarily obscure the present invention.

For the purpose of illustrating the present invention, exemplary embodiments are described with reference to FIGS. 1-7.

In this specification and the appended claims, the singular forms "a," "an," and "the" include plural references unless the context clearly dictates otherwise. Unless defined otherwise, all technical and scientific terms used herein have the same meaning as commonly understood to one of ordinary skill in the art to which this invention belongs.

Figure 1:
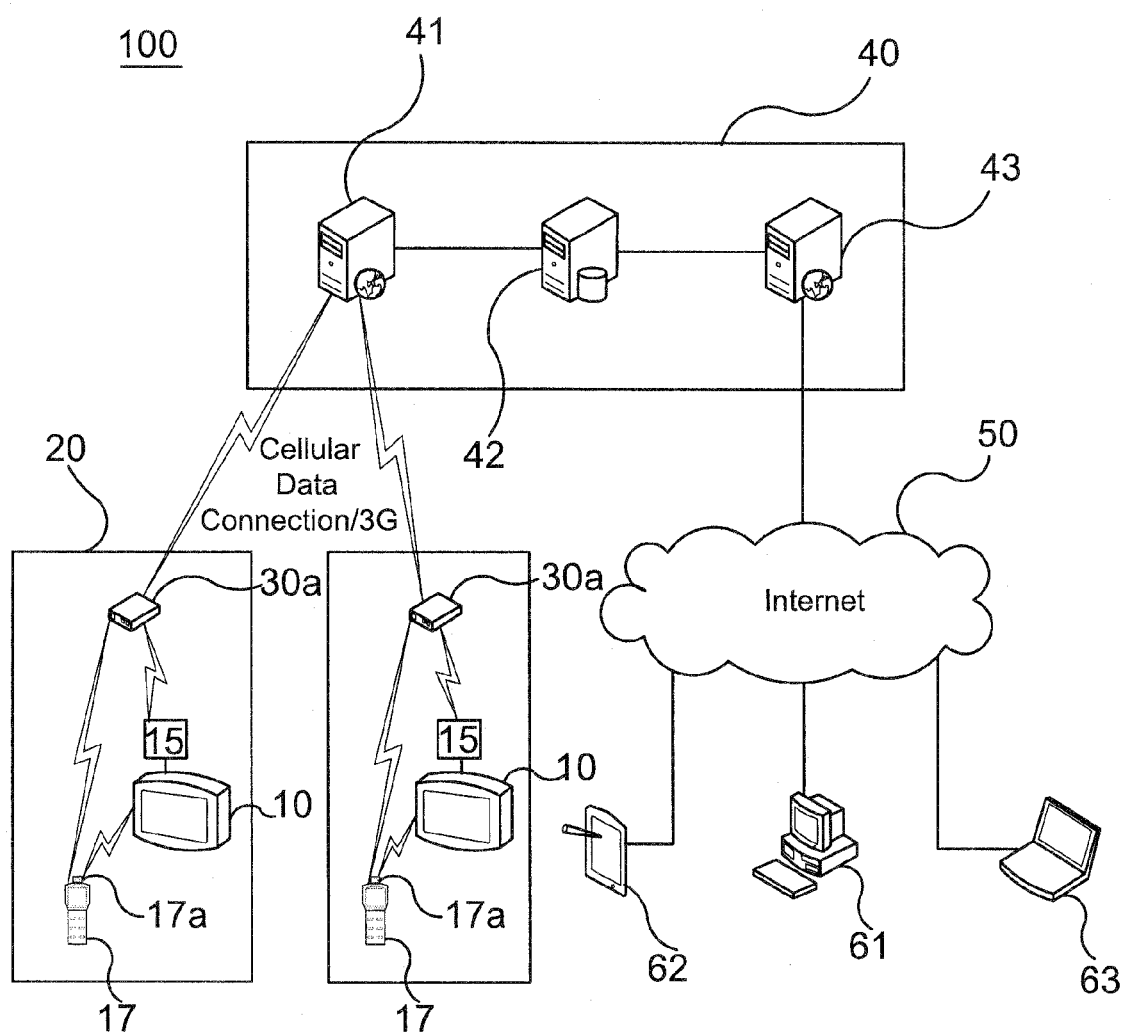
FIG. 1 presents a block diagram of an exemplary network architecture for a remote monitoring system according to the present invention.

A diagram of an exemplary architecture 100 for a system for monitoring medical devices in accordance with the present invention is illustrated in FIG. 1. One or more medical devices 10 are provided at a patient facility 20 for monitoring the medical condition and/or administering medical treatment to one or more patients. Patient facility 20 may comprise a critical care health service center (for example, including hospitals, clinics, assisted living centers and the like) servicing a number of patients, a home facility for servicing one or more patients, or a personal enclosure (for example, a backpack) that may be attached to or worn by an ambulatory patient. Associated with each medical device 10 is an interface circuit 15 that includes a transceiver having one or more of a transmitter and/or a receiver for respectively transmitting and receiving signals in a facility-oriented wireless network such as, for example, a Low-Rate Wireless Personal Area Networks or "LR-WPAN," ZIGBEE network or another low-power personal area network such as a low power BLUETOOTH network, existing or presently under development or consideration. See, e.g., Houda Labiod et al., *Wi-Fi, Bluetooth, Zigbee and WiMax*, Springer 2010, which is incorporated by reference herein in its entirety. It should be understood that interface circuit 15 may be contained within or disposed external to medical device 10 in accordance with the present invention. Also provided within the patient facility 20 are one or more relay modules 30a.

Figure 3A:
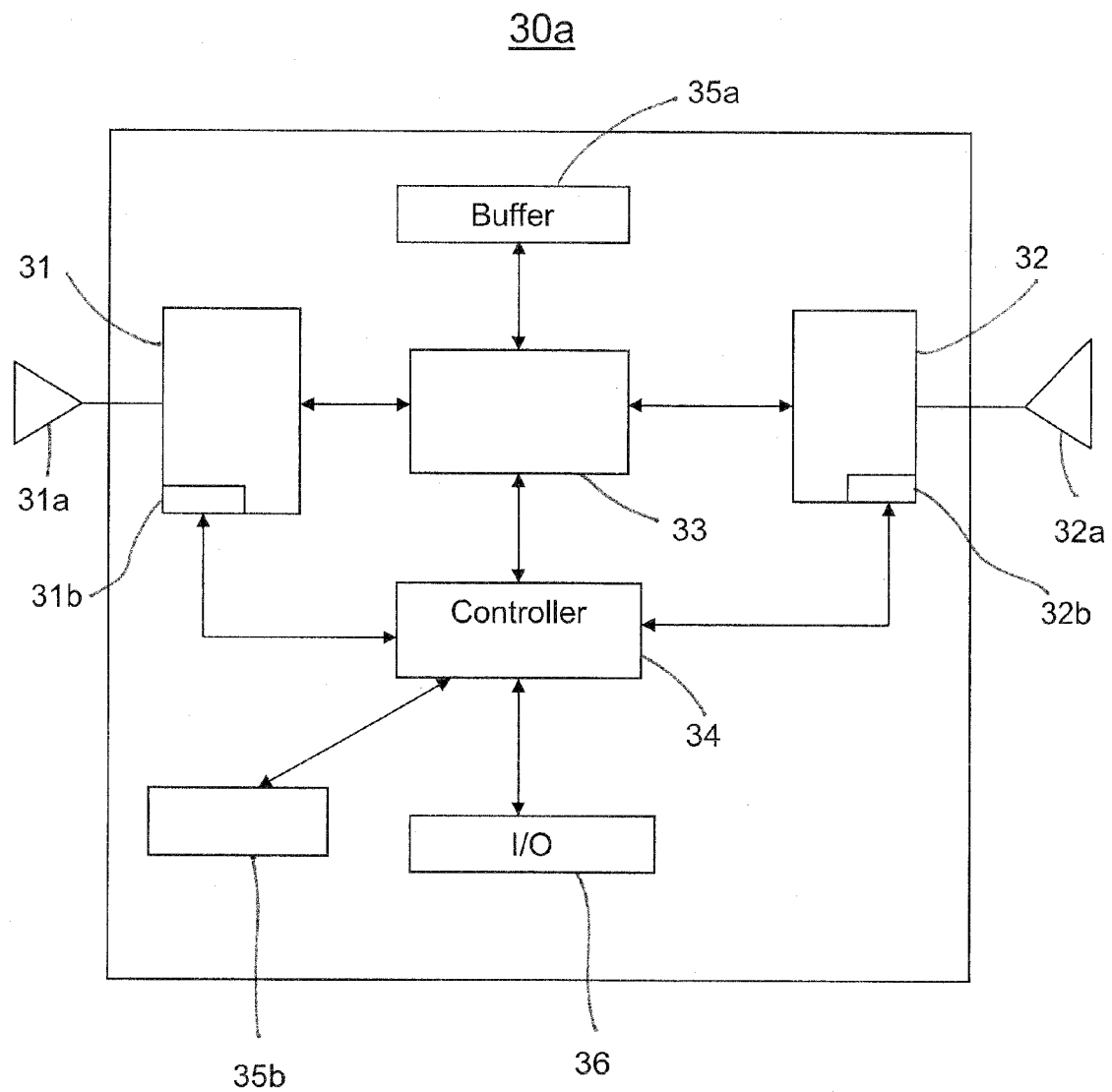
FIG. 3(a) presents a schematic diagram illustrating an exemplary wireless relay module according to the present invention.
Figure 3:
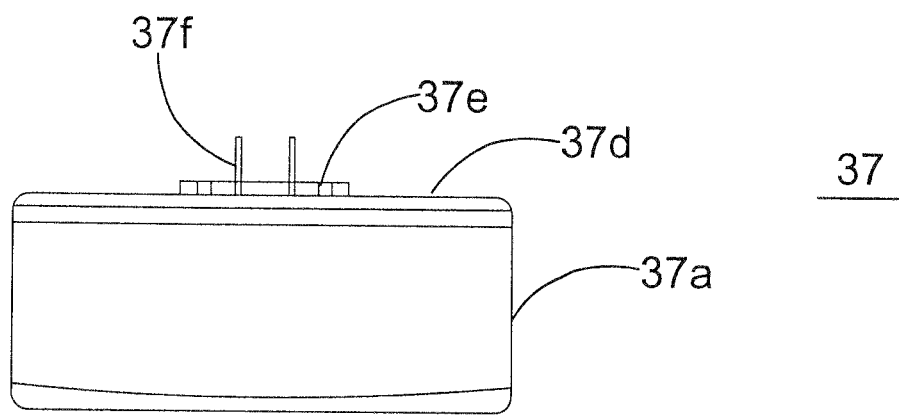
FIGS. 3(b)-3(d) present schematic diagrams respectively illustrating top, front and side views of an embodiment of the wireless relay module of FIG. 3(a)
FIG. 3(e) illustrates an exemplary control panel for the wireless relay module of FIGS. 3(b)-3(d)
Figure 3:
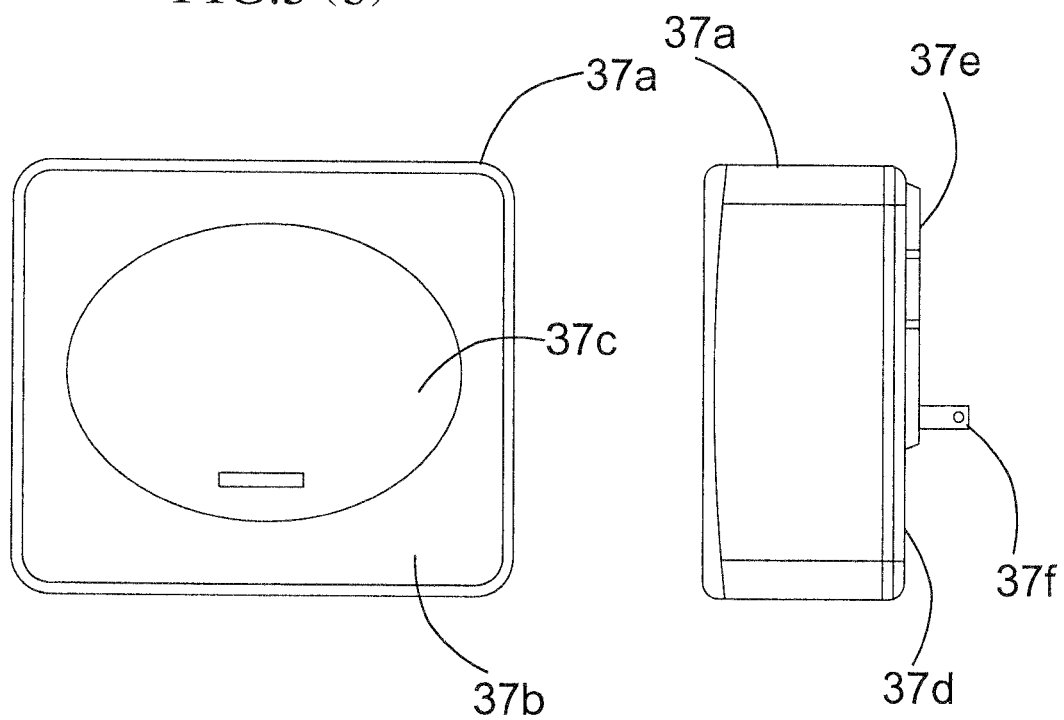

As described in greater detail with regard to FIG. 3(a), each relay module 30a includes a first transceiver 31 for receiving signals from and transmitting signals to the interface circuits 15 or other relay modules 30, 30a in the facility-oriented wireless network. Each relay module 30a, as depicted in FIG. 3(a), further includes a second transceiver 32 for wirelessly transmitting signals to and receiving signals from an access point 40 via a wireless wide-area network or "WWAN". Suitable WWANs for use with the present invention may include, for example, networks based on a Global System for Mobile Communications (GSM) or Code Division Multiple Access (CDMA) cellular network or associated with the 2G, 3G, 3G Long Term Evolution, 4G, WiMAX cellular wireless standards of the International Telecommunication Union Radiocommunication Sector (ITU-R). See, e.g., Vijay Garg, *Wireless Communications & Networking*, Morgan Kaufmann 2007, which is incorporated by reference herein in its entirety for all purposes. For compliance with HIPAA regulations, communications over each of the facility-oriented wireless networks and WWAN are preferably conducted securely using, for example, using a Secure Sockets Layer (SSL) protocol or a Transport Layer Security (TLS) protocol.

As illustrated in FIG. 1, the exemplary architecture 100 may further include one or more wireless patient identification devices 17 in communication with one or more of the relay modules 30a and/or medical devices 10 in proximity to the patient identification device 17 via the interface circuits 15 and 17a operating over the facility-oriented wireless network. Alternatively, a wireless patient identification receiver may be integrated with each medical device 10, and access the facility-oriented wireless network via an associated interface circuit 15. The wireless patient identification devices 17 each receive patient identification data from a patient in proximity to the device 17 that uniquely identifies the patient using one of a variety of commercially-available sensors. For example, each patient identification device 17 may include a camera or other optical scanner and associated circuitry for sensing a barcode (for example, a UPC code or a QR matrix barcode) attached to or otherwise uniquely associated with a patient, such as a patient's wristband. Alternatively, each patient identification receiver 17 may include a radio-frequency identification (RFID) sensor and associated circuitry for sensing an RFID tag embedded in the patient wristband, or another commercially-available radio-frequency sensor capable of sensing an identification signal generated by a radio-frequency transmitter embedded in the patient wristband or otherwise provided as attached to or in proximity to the patient. Finally, each device 17 may in addition or instead include a commercially-available biometric sensor and associated circuitry for patient identification (for example, including one or more of a fingerprint reader, a retinal scanner or a vein-pattern scanner).

For improved efficiencies in centralized monitoring of critical care and home care health service centers, it may be desirable to provide a single "off-site" centralized monitoring location for monitoring several geographically-dispersed critical care health service centers. The exemplary architecture 100 of FIG. 1 has a suitable access point 40 that includes an inbound web server 41 that incorporates or otherwise has access to a transceiver for communicating with the relay modules 30a over the WWAN. Medical device data received by the inbound web server 41 over the WWAN is forwarded to a secure data storage server 42, which is configured for example to log the received data in association with identification information of the associated medical devices. An outbound web server 43 is configured, for example, to receive and qualify data retrieval requests submitted by one or more of remote monitoring devices 61, 62 and 63 over a broad-band network 50 (for example, over the Internet), to request associated medical device data to be retrieved from the secure data storage server 42, and to format and transmit the retrieved medical device data to the one or more remote monitoring devices 61, 62 and 63 for display on associated device displays. It should be understood that any architecture for the access point 40 that enables the receipt, storage and retrieval of medical device data on a device display of the one or more remote monitoring devices 61, 62 and 63 is suitable for use in conjunction with the present invention. As was previously described infra, "medical device data" and "data" as generally used herein means data from or about the medical device including, for example, medical device identification, medical device software, medical device settings or status information (including alarm information and/or alarm priority), patient identification information, patient personal identification number(s) "PIN(s)", patient prescriptions, and/or patient medical and/or physiological data as is collected, produced and/or generated by at least one of the medical device and patient identification device.

Thus, and as will be further described herein with reference to FIGS. 2-7, the remote monitoring system of FIG. 1 is capable of obtaining patient identification information to be associated with a particular medical device, securely transmitting the patient identification information with medical device identification information of the associated medical device to verify that the association of the patient with the medical device is authorized, and beginning operation of the medical device and monitoring of medical data generated by the medical device once authorization has been received.

Figure 2:
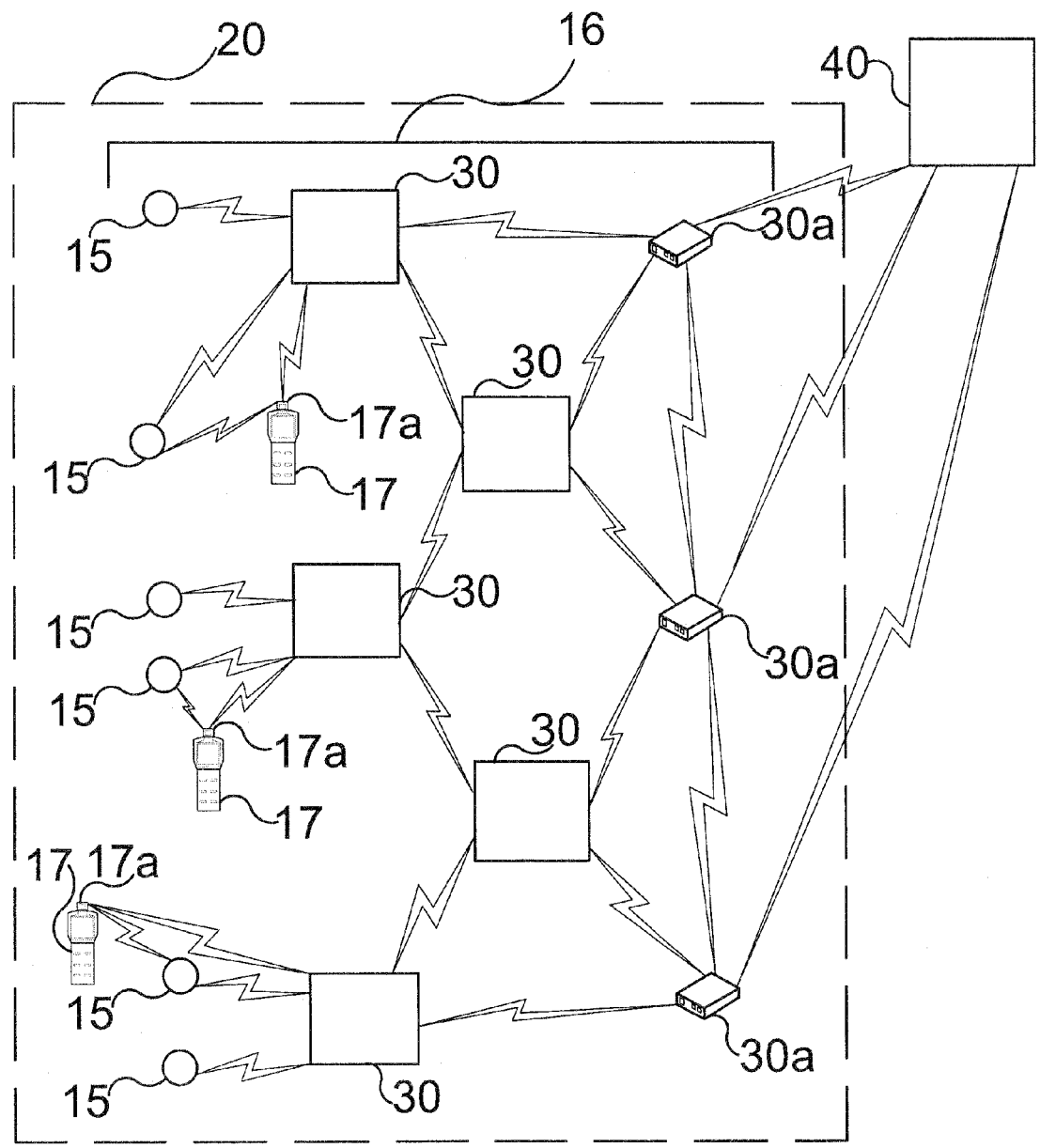
FIG. 2 presents a block diagram further illustrating exemplary wireless network components of the architecture according to FIG. 1.

FIG. 2 presents a block diagram that further illustrates exemplary components of the inventive architecture that are located within or otherwise associated with the patient facility 20 of FIG. 1. In FIG. 2, a number of interface circuits 15, 17a and relay modules 30, 30a are arranged in a wireless relay network 16 within the patient facility 20. The interface circuits 15, 17a and relay modules 30, 30a are configured to communicate with one another via associated wireless links. In a preferred embodiment of the present invention represented in FIG. 2, the network 16 is a network based on the IEEE 802.15.4 standard, for example, such as a ZIGBEE network, a WIRELESSHART network and/or a MIWI network. However, the wireless relay network 16 may be organized according to a variety of other wireless local area network (WLAN) or WPAN formats including, for example, WiFi WLANs based on the IEEE 802.11 standard and/or BLUETOOTH WPANs based on the IEEE 802.15.1 standard.

In the illustrated wireless relay network 16, each of the interface circuits 15, 17a includes a communications interface such as, for example, a wired communications interface, to an associated medical device 10 or patient identification device 17. In addition, each of the relay modules 30, 30a includes at least one transceiver configured to communicate with other relay modules 30, 30a in the wireless relay network 16. Relay modules 30a further include at least a second transceiver for communicating over the WWAN with the access point 40.

The use of a ZIGBEE mesh network for network 16 provides the advantages of being self-configurable when one or more interface circuits 15, 17a and/or relay modules 30, 30a are added to the network, and self-healing when one or more interface circuits 15, 17a and/or relay modules 30, 30a are removed from or otherwise disabled in the network. Sub-groupings of the interface circuits 15, 17a and relay modules 30, 30a may be provided in a defined geographic space (for example, on an individual floor or within a region of a floor in a multi-floor home or care facility).

FIG. 3(a) provides a block diagram illustrating exemplary components of a relay module 30a. The relay module 30a of FIG. 3(a) includes a first transceiver 31 for wirelessly communicating with interface circuits 15, 17a and other relay modules 30, 30a in the WLAN or WPAN network 16 of FIG. 2 via an antenna 31a. The relay module 30a further includes a second transceiver 32 for wirelessly communicating with the access point 40 over the WWAN via an antenna 32a. Each of the transceivers 31, 32 is in communication with a data processing circuit 33, which is configured to operate under the control of a processor 34 to accept medical device data received by the transceivers 31, 32 and to store the received medical device data at least temporarily in a buffer element 35a. In addition, the data processing circuit 33 is further configured to retrieve data from the buffer element 35a under the direction of the processor 34 and provide the retrieved data to a selected one of the transceiver 31 or transceiver 32 for transmission. One or more of the data processing circuit 33 and/or controller 34 may also preferably include commercially available encryption circuitry for encrypting data to be sent by the transceivers 31, 32 and to decrypt data received by the transceivers 31, 32, in accordance for example with HIPAA requirements.

In order to make a selection, the processor 34 is configured to communicate with respective status modules 31b, 32b of the transceivers 31, 32 in order to determine a communications status of each of the transceivers 31, 32. Longer term data storage may preferably be provided by a memory 35b, for example storing instructions for the controller 34, data encryption/decryption software for one of more of the data processing circuit 33 and/or controller 34, a patient identification directory identifying patients using each of the medical devices 10, and the like.

The processor 34 is also preferably in communication with an input/output circuit 36, which provides signals to one or more display elements of the relay module 30a, for example, for indicating a start-up or current status of the relay module 30a, including communication or connection status with the WLAN or WPAN network 16 and WWAN. Input/output circuit 36 may also be configured to provide signals to indicate an A/C power loss, and or to be responsive to signals provided by one or more input devices provided in proximity to the one or more display elements.

Relay module 30a may preferably be provided as a small physical enclosure with an integral power plug and power supply circuit, such that the relay module 30a may be directly plugged into, externally powered and physically supported by a conventional wall outlet providing commercial A/C power. Relay module 30a may also preferably include a battery back-up circuit (not shown) to provide uninterrupted power in the event of A/C power outage of short duration. Battery back-up may also be advantageous, for example, for using the relay module 30a in an ambulatory mode that enables the patient to move within and potentially at a distance from the facility 20, for example, with a medical device 10 that is an ambulatory enteral feeding device. In this configuration, for example, the medical device 10, the interface circuit 15 and relay module 30 may be conveniently carried in a patient-wearable backpack.

FIGS. 3(b)-3(d) respectively illustrate top, front and side views of an exemplary configuration 37 for the relay module 30a. Configuration 37 includes a housing 37a, which is shown in FIGS. 3(b)-3(d) configured essentially as a rectangular box or prism. It should however be noted that the housing may alternatively be configured in any of a variety of three-dimensional shapes having a sufficient interior volume for housing the associated circuits, having a sufficient area 37c on a front panel 37b of the housing 37a for locating a control panel 38 (as further illustrated in FIG. 3(e)), and having a sufficient area on a rear panel 37d for providing a receptacle support 37e and power plug 37f for supportably plugging the module configuration 37 into a conventional power outlet. The power plug 37f may also be provided in a modular and replaceably removable configuration enabling power plugs 37f to be configured according to a variety of international standards to be easily provided to the configuration 37.

Figure 3E:
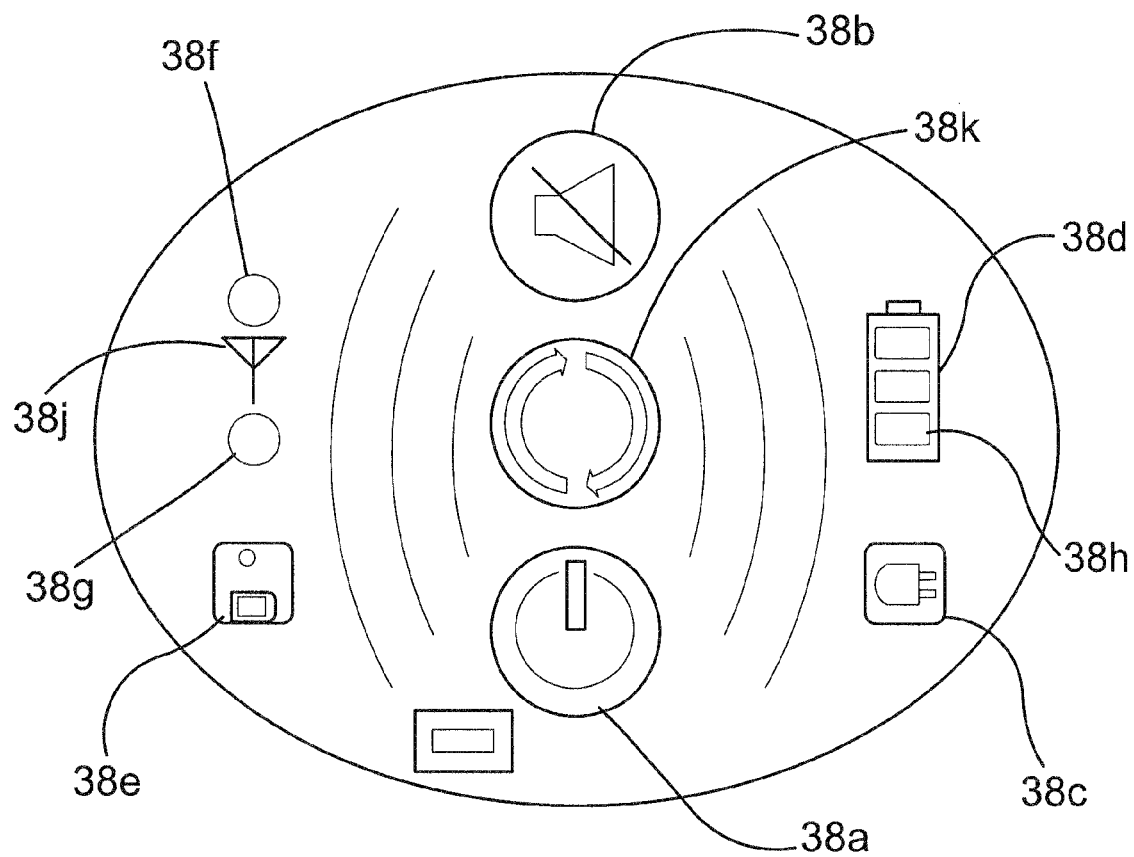

FIG. 3(e) illustrates an exemplary control panel 38 of module configuration 37. The exemplary control panel 38 preferably includes, for example, a power switch 38a for powering and/or de-powering the module configuration 37 after it has been plugged into the conventional wall outlet or equipped with a charged battery back-up subsystem. In addition, the control panel 38 preferably includes an alarm switch 38b which allows a user to mute and/or de-mute an audible alarm (for example, a conventional buzzer, not shown) which is coupled to an alarm circuit (not shown) that is configured to issue an alarm when A/C power to the module configuration 37 has been interrupted and/or when other medical device or remote monitoring system-level alarms occur. The control panel 38 also includes an A/C power indicator 38c which may preferably be provided as one or more light-emitting diode (LED) indicator segments which are activated when A/C power has been provided to the module configuration 37. Optionally, the indicator 38c may be intermittently activated when A/C power is lost (for example, by means of back-up battery power) to signal the loss of A/C power.

The exemplary control panel 38 of FIG. 3(e) also includes a battery indicator 38d to indicate a status of the battery back-up circuit. For example, and as illustrated in FIG. 3(e), the battery indicator 38d may preferably include indicator segments 38h which may be selectively activated to indicate a capacity of the back-up battery. Indicator segments 38h may also be preferably provided as LED segments. Each of the segments 38h may, for example, be activated to indicate that the back-up battery is fully charged, and ones of the segments 38h may be progressively deactivated (for example, proceeding downwardly from an uppermost one of the segments 38h) as battery power is drawn down. In the event that remaining battery power is insufficient to operate the module configuration 37, each of the segments 38 may be deactivated. Alternatively, the indicator segments 38h may be provided as multicolor LED segments (for example, red and green), and ones of the segments 38h be illuminated as green and progressively deactivated until reaching a first low power threshold, and then illuminated as red and progressively activated as power is further diminished so that all LED segments are illuminated when battery power is no longer sufficient to power the module configuration 37.

As further illustrated in FIG. 3(e), the control panel 38 may further include an indicator 38e to indicate a status of the WLAN or WPAN network 16. Similarly to the A/C power indicator 38c, the WLAN/WPAN network status indicator 38e may be activated when the WLAN/WPAN network status is active or accessible, and either de-activated or intermittently activated when the WLAN/WPAN network status is inactive or inaccessible. Finally, a WWAN indicator 38j may be provided to indicate a status of access to the WWAN network. As depicted in FIG. 3(e), the indicator 38j includes indicator elements 38f, 38g for indicating the WWAN network status. In this configuration, for example, the indicator element 38f may be configured with a green LED indicator element that is activated when the WWAN network status is active or accessible, and the indicator element 38g may be configured with a red LED indicator element that is activated when the WWAN network is inactive or inaccessible (for example, when a signal strength of the WWAN network available to the module configuration 37 is insufficient to support communications). Optionally, the indicator element 38f may be intermittently activated when the signal strength of the WWAN network available to the module configuration 37 is marginally sufficient to support communications. Alternatively or in addition, one or more of elements 38f, 38g may each comprise a single bi-color LED. Indicators of the module configuration 37 such as indicators 38e-38h and 38j may be electrically connected to the input-output circuit 36 depicted in FIG. 3(a).

In addition, the control panel 38 may optionally include microphone and speaker elements (not shown) that enable the module configuration 37 to be operated in a voice communication mode to allow for voice communication, for example, between an operator and a help desk technician in event of a trouble condition reported by one of the medical devices 10. Alternatively or in addition, the control panel 38 may include one or more of a camera element (not shown) and/or a display element (not shown) to be operated in a visual communication mode. For example, the camera element may be used to transfer images from displays of one or more medical devices 10 to one of the remote monitoring devices 61, 62 and 63 of FIG. 1, or alternatively or in addition as a patient identification device as father described herein. Finally, the control panel 38 may include a synchronization switch 38k, which may be used as further described herein to initiate a process for associating patient identification information with identification information of a medical device 10.

Figure 4:
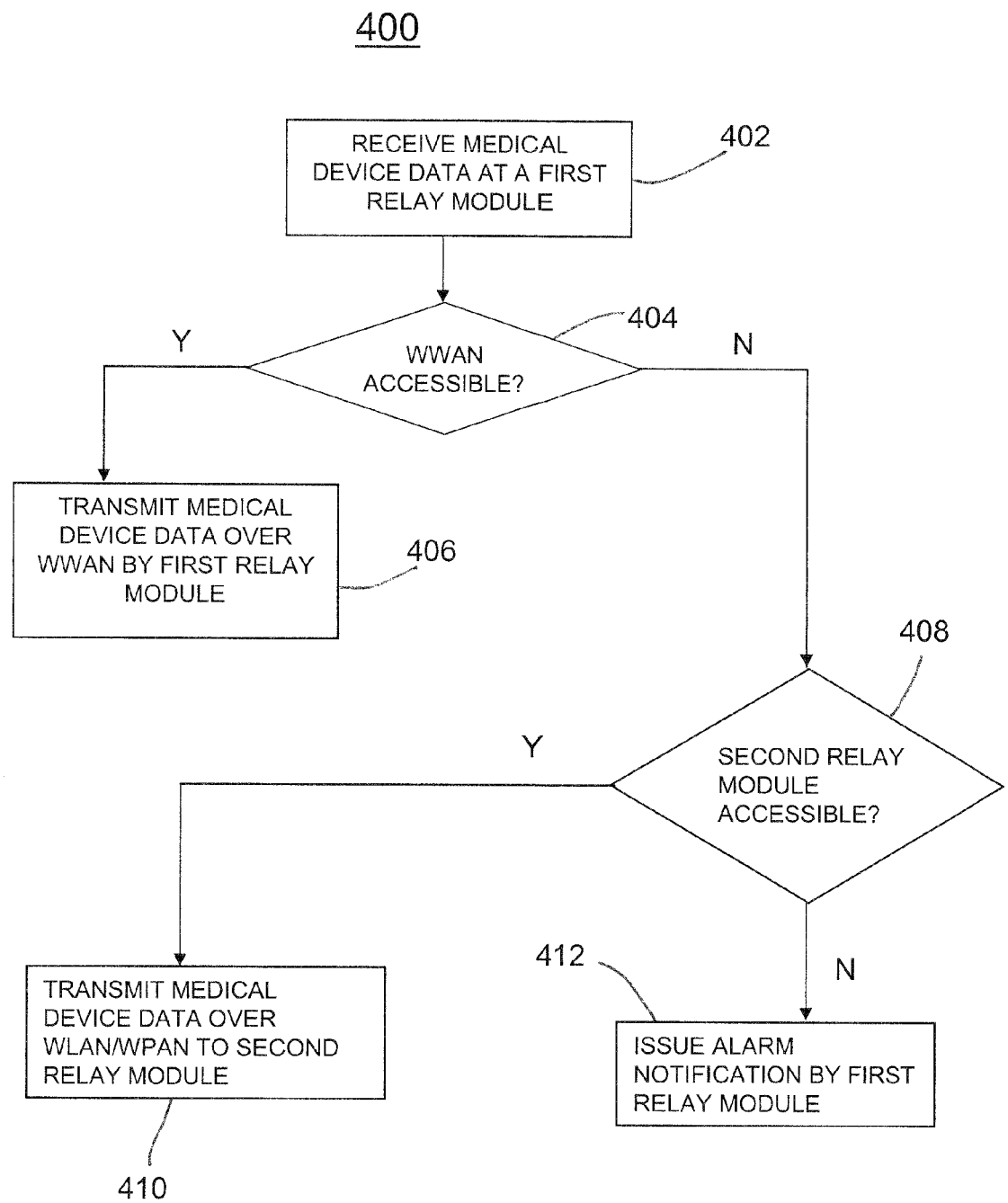
FIG. 4 presents a flow diagram illustrating a first exemplary method of operation for the relay module of FIG. 3(a)

FIG. 4 presents a flow diagram 400 illustrating an exemplary method of operation for the architecture according to FIG. 1 and relay module 30, 30a components of FIGS. 2 and 3(a), relating to the transmission of medical device data obtained from a medical device 10 to the access point 40. First, at step 402 of the method 400, the medical device data is received at a first one of the relay modules 30a from one of the interface circuits 15 and/or other relay modules 30, 30a over the wireless relay network 16. At step 404, the processor 34 of the one relay module 30a determines whether the WWAN is accessible by that relay module 30a.

The determination of step 404 may be carried out in a variety of manners. For example, the processor 34 may interrogate the status module 32b of the transceiver 32 at the time of the receipt of the medical device data to determine a status of access for the transceiver 32 to the WWAN (for example, as the result of the transceiver 32 detecting an access signal of the WWAN having adequate signal strength). Alternatively, the processor 34 may interrogate the status module 32b at a different time including, for example, at system start-up and/or intermittently or periodically (for example, hourly), and maintain a status indicator such as in the buffer element 35a or another storage element to be retrieved at the time of receipt of the medical data. As yet another alternative, the relay module 30, 30a may be assigned a predetermined, fixed role within the network 16. For example, relay modules 30a in the network 16 may be assigned a data routing assignments by a controller or "master" relay module. By definition, the WWAN status for relay module 30 that does not possess WWAN access capability shall have a fixed status of "WWAN inaccessible."

If, as provided for in step 404, the status module 32b indicates that the WWAN is accessible by the transceiver 32, the processor 34 will proceed to step 406 to instruct the data processing circuit 33 of the one relay module 30 to retrieve the medical device data from the buffer element 35a (as necessary) and forward the medical device data to the transceiver 32 for transmission to the access point 40 over the WWAN.

Alternatively, in step 404, the status module 32b may indicate that the WWAN is not accessible by the transceiver 32. For example, if the one relay module 30a is located on a basement floor of the building in an area that is substantially shielded with respect to WWAN signals, the WWAN may not be accessible to the one relay module 30a. In this event, at step 408, the processor 34 determines whether a second relay module 30a is accessible via the WLAN or WPAN. Again, this determination may be made in a variety of manners including by instructing the transceiver 31 to send a handshake signal transmission directed to a second relay module 30a and to listen for a reply, or by retrieving a stored status indicator for the second relay module 30a.

If the second relay module 30a is accessible, then the processor 34 instructs the data processing circuit 33 of the one relay module 30a to retrieve the medical device data from the buffer element 35a (as necessary) and forward the medical device data to the transceiver 31 for transmission to the second relay module 30a over the WLAN or WPAN at step 410. Alternatively, if the second relay module 30a is inaccessible in step 408, this portion of the process 400 may preferably be repeated to search for a further relay module 30a that is accessible. Alternatively, or in the event that no other relay module 30a is available, the processor 34 of the one relay module 30a may preferably issue an alarm notification at step 412. Such an alarm notification may, for example, include one or more of local visual and audio alarms as directed by processor 34 via the input/output circuit 36 of the one relay module 30a, alarm messages directed by the processor 34 to another accessible WPAN, WLAN or WWAN via one or more of the transceivers 31, 32, and/or alarm messages generated by the inbound web server 41 of the access point 40 of FIG. 1 after a specified time period has been exceeded during which a handshake signal of the relay module 30a is due to be received at the inbound web server 41.

Figure 5:
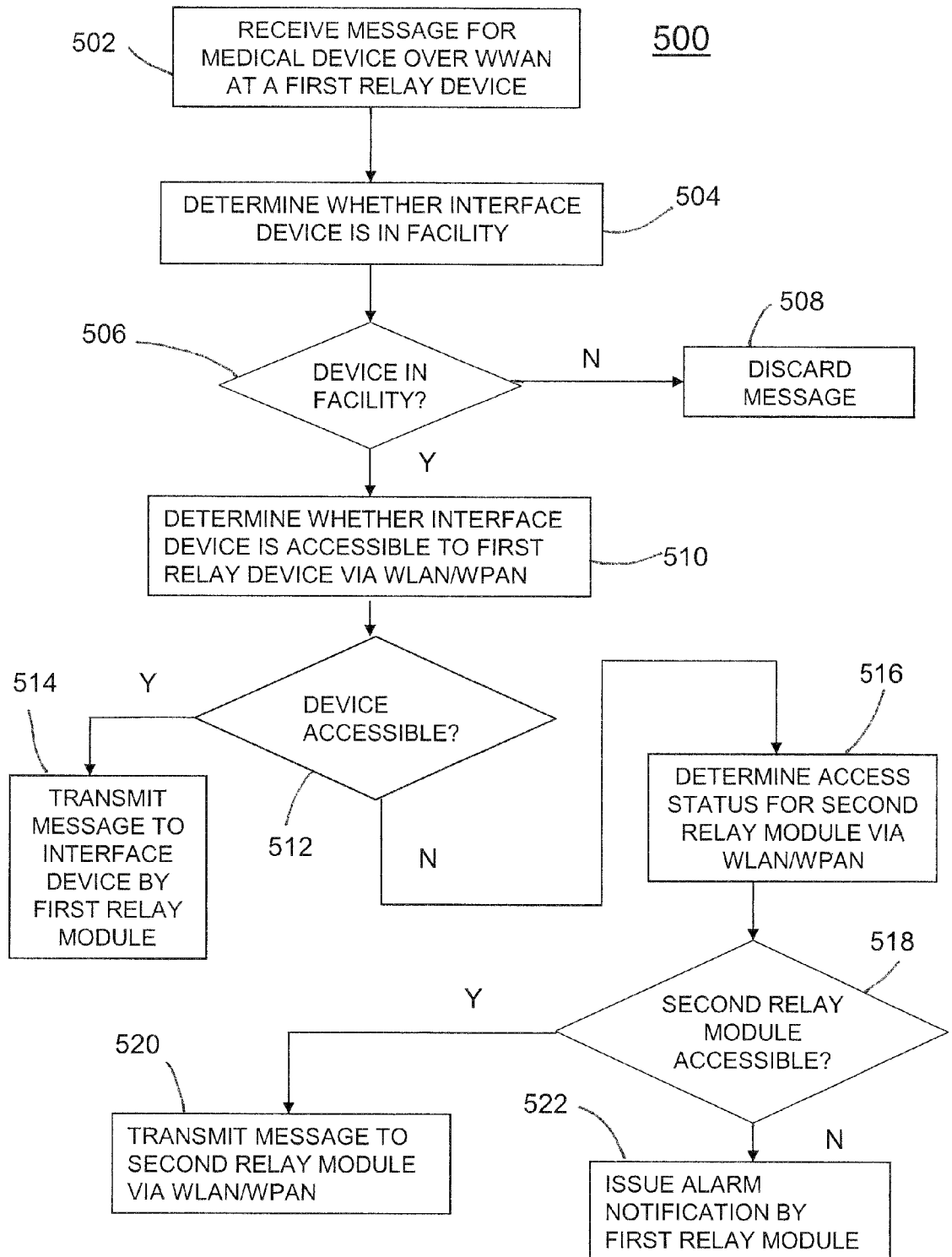
FIG. 5 presents a flow diagram illustrating a second exemplary method of operation for the relay module of FIG. 3(a)

FIG. 5 presents a flow diagram 500 illustrating another exemplary method of operation 500 for the architecture according to FIG. 1, relating to the transmission of a message from the access point 40 to be received by one of the medical devices 10. This enables the access point 40, for example, to communicate with medical devices in order to download new firmware or software, to respond to error messages initiated by the medical devices (for example, to re-set a device or remove it from service, or to run device diagnostics), and to operate the medical device (for example, to adjust a flow rate on a feeding pump).

At step 502 of the method 500, the message is received at the first one of the relay modules 30a from the access point 40 via the WWAN. At step 504, the one relay module 30 determines whether the message is intended to reach one of the interface circuits 15, 17a and/or other relay modules 30, 30a located in the facility 20. This may be accomplished, for example, by maintaining a list of active interface devices 15, 17a and modules 30, 30a in the buffer element 35a or in a manner otherwise accessible to the one relay module 30a, or coding an identifier of the interface device 15, 17a or module 30, 30a to include an identity of the facility 20 that is stored in the buffer element 35a or is otherwise identifiable to the one relay module 30.

If the one relay module 30a determines at step 506 that the interface device 15, 17a or module 30, 30a is not located in the facility, the one relay module 30 may preferably proceed to discard the message at step 508, and/or alternatively alert the access point 40 with a non-delivery message. If the interface device 15, 17a is located in the facility 20, the one relay module 30a determines at step 510 whether the interface device 15, 17a or relay module 30, 30a accessible to the one relay device 30a via the WLAN or WPAN (for example, by consulting a list stored in the buffer element 35a or that is otherwise accessible to the one relay module 30a, or by instructing the transceiver 31 to send a handshake transmission directed to the interface device 15, 17a and to listen for a reply).

If the one relay module 30a determines at step 512 that the interface device 15, 17a or relay module 30, 30a is accessible, then at step 514, it transmits the message via network 16 to that device 15, 17a or relay module 30, 30a via the transceiver 31. In this case, the message may again be broadcasted to all interface devices 15, 17a and modules 30, 30a in communication with the one relay module 30a, and each device 15, 17a or module 30, 30a may decide to act on or ignore the message (for example, by matching to an associated identifier for a medical device 10 or patient identification device 17, or other identifier in the message). If the one relay module 30a alternatively determines at step 512 that the interface device 15, 17a or relay module 30, 301 is not accessible, then it proceeds at step 516 to determine whether a second relay module 30, 30a is accessible via the WLAN or WPAN (for example, by instructing the transceiver 31 to send a handshake transmission directed to the second relay module and to listen for a reply). If the second relay module 30, 30a is available, then the one relay module 30 forwards the message to the transceiver 31 for transmission to the second relay module 30, 30a over the WLAN or WPAN. If the second relay module 30, 30a is inaccessible, then this portion of the process 500 may preferably be repeated to search for a third relay module 30, 30a that is accessible while medical device data remains stored in, for example, buffer element 35a. Alternatively, or in the event that no other relay module 30, 30a is available, the one relay module 30 may preferably issue an alarm notification at step 522, preferably in one of the same manners described above in reference to the method 400 of FIG. 4. Once the message is received by an interface device 15, 17a for an intended medical device 10 or patient identification device 17, the interface device 15, 17a preferably broadcasts a confirmation message to nearby relay modules 30, 30a for forwarding to access point 40.

Figure 6:
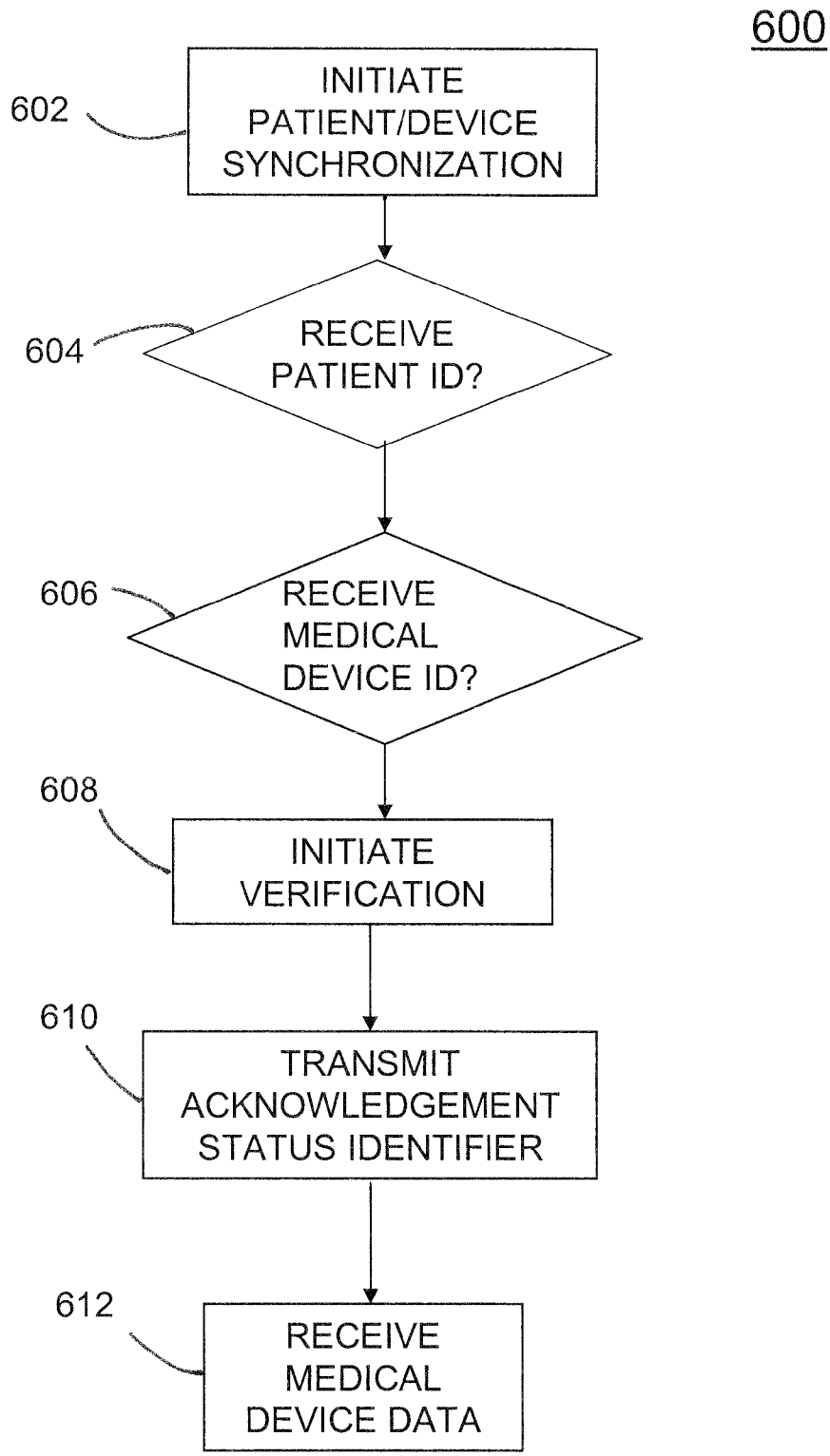
FIG. 6 presents a flow diagram illustrating a third exemplary method of operation for the relay module of FIG. 3(a)

FIG. 6 presents a flow diagram illustrating an exemplary method 600 of identifying a patient that is associated with (that is, intends to receive treatment from or provide patient identification information and/or patient medical and/or physiological data to) a medical device 10 (as depicted, for example, in FIG. 1). At step 602, the process may be initiated, for example, by actuating the synchronization switch 38k on the control panel 38 as illustrated in FIG. 3(e) of a relay module 30a in proximity to the medical device 10. The relay module 30a enters an identification signal reception mode, in which it waits for a first predetermined interval (for example, using a time-out algorithm) at step 604 to receive patient identification data over the facility-oriented wireless network via the interface device 17a of a patient identification device 17. The relay module 30a preferably indicates receipt by presenting an audible or visual signal at the control panel 38, or by broadcasting a receipt signal to the patient identification device 17 over the facility-oriented wireless network.

At step 606, after receipt of the patient identification information, the relay module 30a waits for a second predetermined interval to receive medical device identification information over the facility-oriented wireless network via the interface circuit 15 of a medical device 10. Once again, the relay module 30a preferably indicates receipt of this medical device data by presenting an audible or visual signal at the control panel 38, or by broadcasting a receipt signal to medical device 10 over the facility-oriented wireless network. It should be understood that the order of receipt of the patient identification data and the medical device identification information (which may be respectively transmitted, for example, by a caregiver operating the patient identification device 17 and the medical device 10) may be inverted. In addition, the inventive process 600 may optionally first require the caregiver to transmit caregiver identification data (for example, via one of the patient identification device 17 or the medical device 10, or via a sensor provided in the relay module 30a) which is validated by comparison to a caregiver identification table maintained for example in the memory 35b of the relay module 30a, or alternatively by forwarding a validation request to the remote monitoring system at the access point 40 over one or more of the facility-oriented wireless network and WWAN via an associated one of the transceivers 31, 32.

At step 608, upon receipt of each of the patient identification data and the medical device identification data, a verification process is initiated. This process is carried out by the exemplary method 700 illustrated in the flow diagram of FIG. 7.

Figure 7:
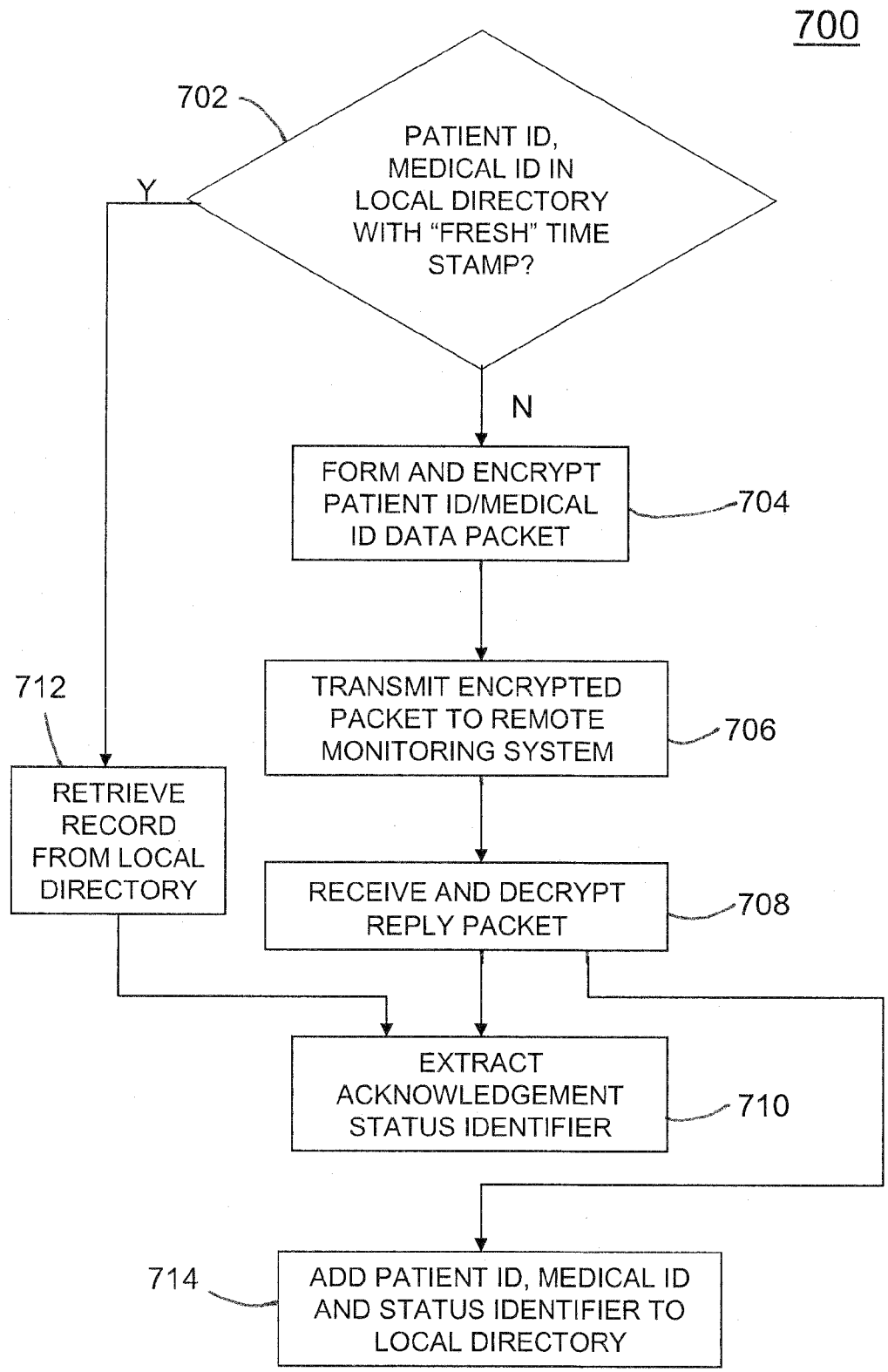
FIG. 7 presents a flow diagram further illustrating elements of the exemplary method of FIG. 6.

At step 702 of FIG. 7, a patient identification directory in the memory 35b of the relay module 30a is interrogated to determine whether a record is present including the received patient identification data and medical device information data, and if so, whether this record includes a "fresh" time stamp indicating that the record is current (for example, if patient identification is verified on a daily basis, a time stamp during the current day). If the time stamp is current, the record is retrieved from the patient identification directory at step 712, and an acknowledgement status identified is extracted from the record at step 710.

If the patient identification data and medical device identification data are not present in the patient identification directory, or if the time stamp does not indicate that a record including such data is current, the relay module 30a proceeds to form a data packet including the patient identification information and medical device identification and to encrypt this packet (for example, using a suitable conventional encryption algorithm such as secure sockets layer (SSL) data encryption) at step 704, and then transmits the encrypted data packet at step 706 for further validation to the remote monitoring system at the access point 40 over one or more of the facility-oriented wireless network and WWAN via an associated one of the transceivers 31, 32. Alternatively, the patient identification information and/or the medical device identification information may be encrypted by one or more of the patient identification information device or the medical device, and steps 702, 704 and 712 may be omitted.

At step 708, the relay module receives a reply packet from the remote monitoring system via one of the transceivers 31, 32, and decrypts that packet. At step 710, the relay module 30a extracts the acknowledgement status identifier from the decrypted packet. At step 714, the relay module 30a preferably adds a record to the patient identification directory in the memory 35b that includes the patient identification information, the medical device identification information, the acknowledgement status identifier and a current time stamp.

Returning to FIG. 6, at step 610, the relay module broadcasts the acknowledgement status identifier (preferably together with at least one of the patient identification data or the medical device identification data) via the transceiver 31 to the medical device 10. Upon receipt of the acknowledgement status identifier, the medical device 10 begins operation and transmits medical device data via an associated interface circuit 15 over the facility-oriented wireless network for receipt by the wireless network 30a at step 612. The acknowledgement status identifier may preferably be encoded to instruct the medical device 10 to operate with predefined operating parameters. Optionally and alternatively, and before beginning operation, the medical device 10 may transmit a request via the interface circuit 15 to confirm preset operating parameters and/or request additional information. Once the operating parameters are confirmed and operation of the medical device 10 begins, the wireless network 30a may operate according to the previously-described processes 400, 500 of FIGS. 4, 5.

As illustrated for example in FIG. 2, each rely module 30, 30a is capable of communicating with a number of medical devices 10 over a period of time. It is possible that communications with some of the medical devices 10 are more time-critical with regard to patient safety than others. For example, consider communications with medical devices 10 including each of a thermometer, a feeding pump and a ventilator. In this case, communications with the ventilator would likely be most time-critical among the three medical devices, while communications with the thermometer might be least critical among the three medical devices.

In accordance with the IEEE 802.15.4 standard, if the network 16 is a ZIGBEE mesh network then there is little risk that communications from more than one medical device will contend for simultaneous access to the network 16. The network 16 operates with a protocol in which a transmitting device checks for energy on a wireless bus component of the network 16. If the bus is in use, the transmitting device waits a preselected amount of time before checking again, and only proceeds to transfer data when the energy level suggests that no other transmission is actively underway on the wireless bus. Nevertheless, for circumstances in which medical device data packets transmitted by the medical devices 10 arrive at a relay module 30, 30a at nearly the same time, there may be a need to manage an order of delivery by the relay module 30.

For example, consider a data packet from a ventilator indicating disconnection from a comatose patient, with possible fatality. In this case, the ventilator should be assigned priority for transmitting to one or more of remote monitoring devices 61, 62 and 63, while data transmissions from thermometer and pump are discontinued until a response to the data packet transmitted by the ventilator is received from one of the remote monitoring devices 61, 62 and 63. For example, the ventilator might be assigned a priority of 1, while the feeding pump is assigned a priority of 2 and the thermometer is assigned a priority of 3. The assigned priority is preferably indicated in each data packet transmitted by and to the medical devices, for example, as a "priority nibble."

With reference to FIG. 3(a), the processor 34 may be configured to read the priority nibble from each received data packet, and to instruct the data processing circuit 33 to place the data packet at a logical position in the buffer element 35a based upon the priority designation. For example, critical data packets for the ventilator would be positioned for first retrieval and transmission by the relay module 30, 30a, and other data packets are respectively positioned in order according to their priority.

In addition, under circumstances where urgent commands may need to be transmitted by one of the remote monitoring devices 61, 62 and 63 anticipated based on an urgent data packet from the medical device (ventilator), the wireless relay module 30, 30a may in addition discontinue reception of any new medical device information from other medical devices until the urgent commands are relayed and an associated alarm condition has been terminated or released.

The wireless relay module disclosed herein for providing networked communications between a series of medical devices and a remote monitoring device provides a number of distinct advantages in comparison to other monitoring systems. By employing wireless relay networks such as ZIGBEE networks based on the IEEE 802.15.4 standard, for wireless communications between the medical devices 10 and relay modules 30, 30a in accordance with one embodiment of the invention, power and size requirements can be minimized so that the interface circuits 15 can be easily and inexpensively applied to and/or integrated with the medical devices 10.

By introducing relay modules 30a that are part of the wireless relay networks and are directly able to access off-site monitoring devices via a WWAN, access to and reliance on existing and potentially unreliable LAN facilities at a facility can be avoided. By incorporating relay features into the relay modules 30a that relay communications from a first relay module 30a to a second relay module 30a in the event that WWAN access to the first relay module 30a has been compromised, the present invention improves reliability and enables the use of conventional, low-cost cellular transceivers in the relay modules 30a for accessing the WWAN.

It is possible to limit the configuration of cellular transceivers to just the relay modules 30a in a facility, instead of modules 30 and 30a. In addition, by providing the relay modules 30a in a compact enclosure, the relay modules 30a are easily connected to reliable commercial power sources and easily moved when needed to reconfigure the wireless relay networks according to facilities changes. The portability for ambulatory use that is provided by battery back-up is an additional advantage.

It should of course, be understood that while the present invention has been described with respect to disclosed embodiments, numerous variations are possible without departing from the spirit and scope of the present invention as defined in the claims. For example, the present invention may be based on any of a number of current and future WPAN, WLAN and WWAN standards beyond those explicitly described herein. It should also be understood that it is possible to use exclusively relay modules 30a in the WLAN or WPAN network 16 of FIGS. 1 and 2, with transceivers for communicating with other relay modules as well as over the WWAN.

In addition, respective interface circuits useable with the present invention may include components of and perform the functions of the module 30 to provide greater flexibility in accordance with the present invention. Further, numerous configurations of components for relay module 30a are useable with the present invention beyond the components shown in FIG. 3. For instance, an input-output buffer may be used with respective switches under control of a processor for directing medical device data to transceivers 31, 32 as needed. Moreover, it is intended that the scope of the present invention include all other foreseeable equivalents to the elements and structures as described herein and with reference to the drawing figures. Accordingly, the invention is to be limited only by the scope of the claims and their equivalents.

We claim:

1. A patient monitoring system configured for providing communications between medical devices used by patients and a remote monitoring device via an internet-accessible wireless communications network, said system comprising:

a medical device to be used by a patient;

a patient identification device capable of receiving an input indicative of patient identification information of the patient and of transmitting the patient identification information; and at least one relay module comprising:

a first receiver capable of wirelessly receiving data over a wireless relay network;

a second receiver capable of wirelessly receiving data over the internet-accessible wireless communications network a first transmitter capable of wirelessly transmitting the received data to a wireless relay module over the wireless relay network;

a second transmitter capable of wirelessly transmitting the received data over an internet-accessible wireless communications network to the remote monitoring device; and a controller coupled to the first and second transmitters, wherein: one or more of the patient identification device and the medical device are capable of transmitting patient identification data and medical device identification data to the at least one relay module over the wireless relay network, said controller of said at least one relay module is configured to select one of said first transmitter or said second transmitter for transmitting the identification information to the remote monitoring device, said at least one relay module being further configured to receive an acknowledgement status transmitted by the remote monitoring device at one of said first and second receivers, and to transmit the acknowledgement status by said first transmitter to the medical device over the wireless relay network, and the medical device being further configured to receive the acknowledgement status and transmit medical device data corresponding to an output of at least one sensor of the medical device to the at least one relay module via the wireless relay network when the received acknowledgement status represents a particular status.

2. The system of claim 1, wherein the acknowledgment status is received in a first form at one of said first or second receivers of the at least one relay module, and is transmitted in a second form by said first transmitter of the at least one relay module to the medical device.

3. The system of claim 2, wherein said controller is capable of determining a status of said internet-accessible wireless communications network and of selecting one of said first or second transmitter for transmitting said received data based on said status.

4. The system of claim 2, wherein said controller is configured to transmit said received information via the internet-accessible wireless communications network by said second transmitter if said status satisfies a particular criteria; and is configured to transmit said received information by said first transmitter in communication with said wireless relay network if said status fails to satisfy said particular criteria.

5. The system of claim 2, wherein said at least one relay module further comprises: a memory electrically connected to said controller, said memory capable of buffering operating instructions from said remote monitoring device at one of said first and second receivers and said controller capable of controlling at least one of the order and or the priority for transmission of said buffered operating instructions by said first transmitter to the medical device, wherein said at least one relay module is further capable of outputting warnings or error messages concerning a current availability of one or more of the wireless relay network and the internet-accessible wireless communications network.

6. The system of claim 1, wherein said second transmitter is further capable of transmitting operating instructions to said at least one medical device.

7. The system of claim 1, wherein said wireless relay network is a ZIGBEE network.

8. The system of claim 1, wherein said internet-accessible wireless communications network is a mobile communications network.

9. The system of claim 8, wherein said mobile communications network is a CDMA or GSM-based network.

10. The system of claim 1, wherein one or more of the patient identification device and the medical device comprises: a third transmitter capable of wirelessly transmitting said medical device data over said wireless relay network.

11. The system of claim 1, wherein one or more of the patient identification device and the medical device comprises: a third receiver capable of wirelessly receiving instructions over said wireless relay network for execution by said medical device.

12. The system of claim 1, wherein said particular status provides a real-time authorization of use of the medical device by the patient based upon a pre-authorization record for the patient.

13. The system of claim 1, wherein: one or more of the patient identification device, the medical device or the at least one relay module is capable of encrypting the patient identification information prior to transmitting the patient identification information to the remote monitoring device.

14. The system of claim 1, wherein: one or more of the medical device or the at least one relay module are capable of encrypting the medical device identification information prior to transmitting the medical device identification information to the remote monitoring device.

15. The system of claim 1, wherein the patient identification device is coupled to the medical device, and the medical device is capable of receiving the patient identification information from the patient identification device and transmitting the patient identification information to the at least one relay module.

16. The system of claim 1, wherein the wireless relay network is a BLUETOOTH network.

17. The system of claim 15, wherein the medical device is capable of associating the patient identification information with the medical device information.

18. The system of claim 1, wherein said patient identification device further comprises a patient identification information reader for receiving the input indicative of patient identification information.

19. The system of claim 18, wherein the patient identification information reader is coupled to the medical device.

20. The system of claim 18, wherein the patient identification information reader comprises a barcode reader.

21. The system of claim 18, wherein the patient identification information reader comprises a radio frequency identification tag reader.

22. The system of claim 18, wherein the patient identification information reader comprises a device selected from the group consisting of fingerprint readers, retinal readers, vein-pattern scanners and cameras.

23. The system of claim 18, wherein the patient identification information reader comprises a device selected from the group consisting of smartphones, tablet computers, PDA's and PCs.

24. The system of claim 5, wherein said memory of the at least one relay module is further capable of storing one or more of the received patient identification information or the received medical device identification information.

25. The system of claim 1, wherein the at least one relay module is further capable of transmitting the patient identification information and the medical device identification information in a single information block.

26. The system of claim 15, wherein the medical device further comprises a memory and is capable of storing the patient identification information received from the patient identification device in the memory of the medical device.

27. The system of claim 15, wherein the patient identification device is an integral component of or fixedly attached to the medical device.

28. The system of claim 16, wherein the medical device is capable of transmitting the patient identification information and the medical device identification information in a single information block.

* * * * *